(12) United States Patent
Kawabe et al.

(10) Patent No.: US 7,479,484 B2
(45) Date of Patent: *Jan. 20, 2009

(54) PEPTIDES AND PEPTIDOMIMETICS HAVING IMMUNE-MODULATING, ANTI-INFLAMMATORY, AND ANTI-VIRAL ACTIVITY

(75) Inventors: Takumi Kawabe, Numazu (JP); Hidetaka Kobayashi, Numazu (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 343 days.

This patent is subject to a terminal disclaimer.

(21) Appl. No.: 10/877,961

(22) Filed: Jun. 25, 2004

(65) Prior Publication Data

US 2006/0003941 A1    Jan. 5, 2006

Related U.S. Application Data

(60) Provisional application No. 60/482,750, filed on Jun. 25, 2003.

(51) Int. Cl.
*A61K 38/00* (2006.01)
*A01N 37/18* (2006.01)

(52) U.S. Cl. .............................. 514/15; 514/2
(58) Field of Classification Search ........................ None
See application file for complete search history.

(56) References Cited

U.S. PATENT DOCUMENTS 6,239,268 B1 *  5/2001  Lovenberg et al. ......... 536/23.5
6,495,586 B2 * 12/2002  Jacobs et al. ................ 514/411
6,995,135 B2 *  2/2006  Kawabe et al. .............. 514/2
7,125,842 B2 * 10/2006  Kawabe et al. .............. 514/2

FOREIGN PATENT DOCUMENTS

WO    99/15157       4/1999
WO    01/21771       3/2001
WO    03/059942      7/2003
WO    2004/089396   10/2004

OTHER PUBLICATIONS

D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Soussi-Gounni et al. Role of IL-9 in the pathophysiology of allergic diseases. Molecular mechanisms in allergy and clinical immunology. 2001. pp. 575-582.*
Stivahtis et al., "Conservation and Host Specificity of Vpr-Mediated Cell Cycle Arrest Suggest a Fundamental Role in Primate Lentivirus Evolution and Biology", *J. Virol.*, 1997; 71(6): 4331-4338.
Al-Obeidi et al., "Peptide and Peptidomimetic Libraries", *Molecular Biotechnology*, 1998; 9(3):205-223.
Spatola, "Peptide Backbone Modifications: A Structure-Activity Analysis of Peptides Containing Amide Bond Surrogates", *Chemistry and Biochemistry of Amino Acids, Peptides, and Proteins: A Survey of Recent Developments*, vol. 7, 1983; Chap. 5: 267-357.
Subbramanian et al., "Human Immunodeficiency Virus Type 1 Vpr Is a Positive Regulator of Viral Transcription and Infectivity in Primary Human Macrophages", *J. Exp. Med.*, 1998; 187(7): 1103-1111.
Campbell et al., "Vpr of Simian Immunodeficiency Virus of African Green Monkeys Is Required for Replication in Macaque Macrophages and Lymphocytes", *J. Virol.*; 1997; 71(7): 5593-5602.
Caruthers et al., "New chemical methods for synthesizing polynucleotides" *Nucleic Acids Synthesis: Applications to Molecular Biology and Genetic Engineering, Proceedings of the International Symposium on Chemical Synthesis of Nucleic Acids*, held in Egestorf, GFR, on May 5-8, 1980, *Nucleic Acids Symposium Series* No. 7, 1980; 215-223.
Horn et al., "Synthesis of oligonucleotides on cellulose. Part II: design and synthetic strategy to the synthesis of 22 oligodeoxymucleotides coding for Gastric Inhibitory Polypeptide (GIP)", *Nucleic Acids Symposium Series* No. 7, 1980; 225-232.
Fiocchi, "Intestinal inflammation: a complex interplay of immune and nonimmune cell interactions", *Am. J. Physiol. Gastrointest. Liver Physiol.*, 1997; 273:G769-G775.
Jowett et al., "The Human Immunodeficiency Virus Type 1 vpr Gene Arrests Infected T Cells in the $G_2$ + M Phase of the Cell Cycle", *J. Virol.*, 1995; 69(10): 6304-6313.
Frenkel et al., "7,12-Dimethylbenz[A]Anthracene Induces Oxidative DNA Modification in Vivo", *Free Radical Biology & Medicine*, 1995; 19(3): 373-380.
Østergaard et al, "Peptomers: A versatile approach for the preparation of diverse combinatrial peptidomimetic bead libraries", *Molecular Diversity*, 1997; 3: 17-27.
Hruby et al., "Synthesis of oligopeptide and peptidomimetic libraries", *Current Opinion in Chemical Biology*, 1997; 1: 114-119.
Blommers et al., "Effects of the Introduction of L-Nucleotides into DNA. Solution Structure of the Heterochiral Duplex d(G-C-G-(L)T-G-C-G)·d(C-G-C-A-C-G-C) Studied by NMR Spectroscopy", *Biochemistry*, 1994; 33: 7886-7896.
Roberge et al, "A Strategy for a Convergent Synthesis of N-Linked Glycopeptides on a Solid Support", *Science*, 1995; 269(5221): 202-204.
Belousov et al., "Sequence-specific targeting and covalent modification of human genomic DNA", *Nucleic Acids Research*, 1997; 25(17): 3440-3444.

* cited by examiner

*Primary Examiner*—Cecilia Tsang
*Assistant Examiner*—Marcela M Cordero Garcia
(74) *Attorney, Agent, or Firm*—Pillsbury Winthrop Shaw Pittman LLP

(57) ABSTRACT

The invention provides compounds having immune-modulating and/or anti-inflammatory and/or anti-viral activity, wherein compounds of the invention include peptides and peptidomimetics. The invention further provides methods of using immune-modulating and/or anti-inflammatory and/or anti-viral compounds of the invention. In particular, the invention provides methods for treating a disease related to an immune disorder or inflammation or viral infection by administering an amount of a G2-checkpoint-abrogating peptide or peptidomimetic sufficient to inhibit the disease.

10 Claims, 4 Drawing Sheets

| Inhibition of HIV-1 WeJo Replication in PBMC ||||||||||
|---|---|---|---|---|---|---|---|---|---|
| p24 values(pg/mL) ||||||||||
| SF332 (CBP 501) CONC (µg/ml) | 0.00 | 0.313 | 0.625 | 1.250 | 2.500 | 5.00 | 10.00 | 20.00 | 40.00 | 80.0 |
| SAMPLE 1 | 8543 | 4876 | 9709 | 893 | 2400 | 620 | 1011 | 5311 | 132 | 51 |
| SAMPLE 2 | 12345 | 13375 | 3936 | 1063 | 5184 | 7614 | 1432 | 1209 | 183 | 51 |
| SAMPLE 3 | 8095 | 1731 | 2167 | 6853 | 8205 | 4933 | 2466 | 1677 | 103 | 37 |
| MEAN | 9660.8 | 6660.7 | 5270.7 | 2936.3 | 5263.0 | 4389.0 | 1636.3 | 2732.3 | 139.3 | 46.3 |
| % VC | 100.0 | 68.9 | 54.6 | 30.4 | 54.5 | 45.4 | 16.9 | 28.3 | 1.4 | 0.5 |
| TOXICITY VALUES (Cell Titer 96 – O. D. @ 490/650 nm) ||||||||||
| SF332 (CBP 501) CONC (µg/ml) | 0.00 | 0.313 | 0.625 | 1.250 | 2.500 | 5.00 | 10.00 | 20.00 | 40.00 | 80.0 |
| SAMPLE 1 | 0.443 | 0.432 | 0.441 | 0.596 | 0.547 | 0.530 | 0.537 | 0.434 | 0.433 | 0.454 |
| SAMPLE 2 | 0.486 | 0.389 | 0.400 | 0.503 | 0.356 | 0.299 | 0.436 | 0.456 | 0.350 | 0.451 |
| SAMPLE 3 | 0.446 | 0.534 | 0.544 | 0.510 | 0.403 | 0.463 | 0.479 | 0.481 | 0.476 | 0.482 |
| MEAN | 0.458 | 0.452 | 0.462 | 0.536 | 0.435 | 0.430 | 0.484 | 0.457 | 0.420 | 0.462 |
| % CC | 100.0 | 98.6 | 100.8 | 117.0 | 95.0 | 94.0 | 105.6 | 99.8 | 91.6 | 100.9 |
| IC50 (µg/ml) =0.71 | | | TC50 (µg/ml) =>80.0 | | | | TI = >112.68 | | |

FIG. 1a

| Inhibition of HIV-1 Ba-L Replication in human macrophages | | | | | | | | | | |
|---|---|---|---|---|---|---|---|---|---|---|
| p24 Values(pg/mL) | | | | | | | | | | |
| SF332 (CBP 501) CONC (µg/ml) | 0.00 | 0.3125 | 0.625 | 1.250 | 2.500 | 5.00 | 10.00 | 20.00 | 40.00 | 80.0 |
| SAMPLE 1 | 5487 | 3658 | 2697 | 2104 | 3099 | 963 | 2781 | 739 | 519 | 58 |
| SAMPLE 2 | 4656 | 4210 | 4972 | 2411 | 4413 | 4388 | 749 | 2221 | 115 | 81 |
| SAMPLE 3 | 5385 | 4048 | 3549 | 4096 | 4859 | 4073 | 1518 | 278 | 482 | 73 |
| MEAN | 5176.3 | 3971.8 | 3739.4 | 2870.4 | 4123.8 | 3141.3 | 1682.8 | 1079.3 | 372.1 | 70.8 |
| % VC | 100.0 | 76.7 | 72.2 | 55.5 | 79.7 | 60.7 | 32.5 | 20.9 | 7.2 | 1.4 |
| TOXICITY VALUES (Cell Titer 96 - O. D. @ 490/650 nm) | | | | | | | | | | |
| SF332 (CBP 501)CONC (µg/ml) | 0.00 | 0.313 | 0.625 | 1.250 | 2.500 | 5.00 | 10.00 | 20.00 | 40.00 | 80.0 |
| SAMPLE 1 | 1.001 | 0.864 | 0.632 | 0.826 | 0.624 | 0.704 | 0.698 | 0.739 | 0.825 | 0.769 |
| SAMPLE 2 | 1.020 | 0.911 | 0.906 | 0.712 | 0.722 | 0.786 | 0.698 | 0.744 | 0.729 | 0.675 |
| SAMPLE 3 | 1.085 | 0.977 | 0.928 | 0.899 | 0.944 | 0.956 | 0.806 | 0.807 | 0.799 | 0.792 |
| MEAN | 1.035 | 0.917 | 0.822 | 0.812 | 0.763 | 0.816 | 0.734 | 0.763 | 0.784 | 0.745 |
| % CC | 100.0 | 88.6 | 79.4 | 78.5 | 73.7 | 78.8 | 70.9 | 73.8 | 75.8 | 72.0 |

PEPTIDES AND PEPTIDOMIMETICS HAVING IMMUNE-MODULATING, ANTI-INFLAMMATORY, AND ANTI-VIRAL ACTIVITY

RELATED APPLICATIONS

This application claims benefit of priority to U.S. Provisional Patent Application Ser. No. 60/482,750 filed Jun. 25, 2003.

FIELD OF THE INVENTION

The invention relates to peptides and peptidomimetics having immune-modulating activity, anti-inflammatory activity, and anti-viral activity, specifically anti-HIV activity. The invention includes the use of cell cycle G2-checkpoint-abrogating peptides and peptidomimetics as immune-modulating agents, anti-inflammatory agents, and anti-viral agents, specifically anti-HIV agents.

BACKGROUND

Cell-cycle-G2-checkpoint-abrogating peptides have been developed using phenotype-based screening to identify compounds that selectively abrogate the G2 checkpoint, as described in U.S. application Ser. No. 10/347,145, the entire contents of which are hereby incorporated by reference. It was demonstrated that various CBP compounds inhibit phosphorylation activities of variety of kinases involved in the cell cycle G2 checkpoint and bind 14-3-3 proteins involved in the cell cycle G2 checkpoint signal transduction pathways and a variety of other intracellular signal transduction pathways. G2 cell cycle arrest, kinases, and 14-3-3 proteins are involved in a wide variety of other biological processes including immune responses, inflammation, and viral infections.

SUMMARY OF THE INVENTION

The invention provides compounds having immune-modulating and/or anti-inflammatory and/or anti-viral activity, wherein compounds of the invention include peptides and peptidomimetics. The invention further provides methods of using immune-modulating and/or anti-inflammatory and/or anti-viral compounds of the invention.

The invention provides methods for treating a disease characterized by an immune disorder or inflammatory response by administering an amount of a G2-checkpoint-abrogating peptide or peptidomimetic sufficient to inhibit the disease. Compounds of the invention are useful for treating diseases characterized by an immune disorder or inflammatory response diseases, e.g., inflammation, arthritis, auto-immune diseases, collagen diseases, allergy, asthma, or atopy. For example, these compounds can be used to treat subjects, including mammals such as humans, having or at risk of having inflammation, arthritis, auto-immune diseases, collagen diseases, allergy, asthma, pollinosis, or atopy.

The invention method provides a method of treating disease caused by viral infection by administering an amount of a G2-checkpoint-abrogating peptide or peptidomimetic sufficient to inhibit the disease and/or the viral infection. Compounds of the invention are useful for treating diseases caused by viral infection, in particular diseases caused by lentiviruses, especially HIV. For example, these compounds can be used to treat subjects, including mammals such as humans, having or at risk of having viral infection, especially a lentivirus infection, and more especially an HIV infection, and even more especially HIV AIDS.

DESCRIPTION OF DRAWINGS

FIG. 1 shows the inhibition of replication the WeJo strain of HIV-1 in peripheral blood mononuclear cells (PBMC) by administration of CBP501 (SEQ ID NO: 80) at a range of concentrations from 0.3125 µg/ml CBP501 to 80 µg/ml CBP501; FIG. 1A shows the results in table form and FIG. 1B shows the results in graphical form.

FIG. 2 shows the inhibition of replication of the Ba-L strain HIV-1 in human macrophages by administration of CBP501 (SEQ ID NO: 80) at a range of concentrations from 0.3125 µg/ml CBP501 to 80 µg/ml CBP501; FIG. 2A shows the results in table form and FIG. 2B shows the results in graphical form.

Figure 1B:
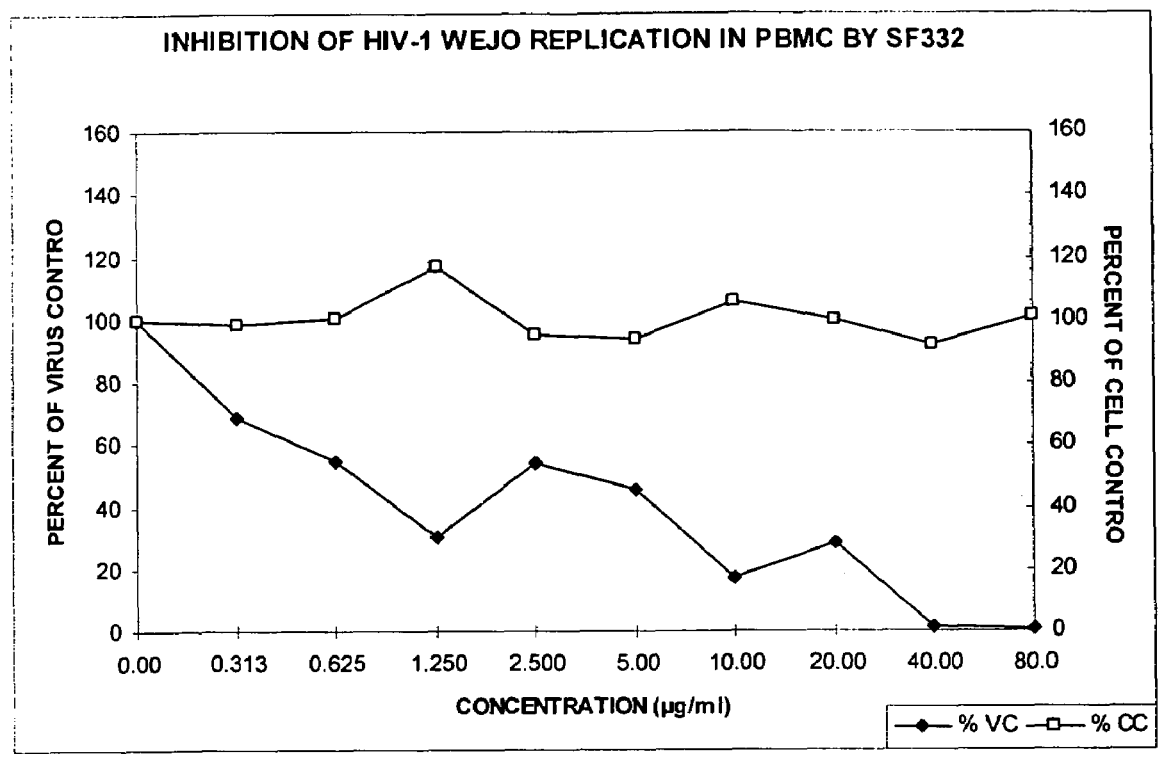

Table 1 shows the effects of intraperitoneal administration of CBP501 on passive cutaneous anaphylaxis (PCA) in rats.

Table 2 shows the effects of intraperitoneal administration of CBP501 on development of adjuvant-induced arthritis in rats.

Table 3 discloses sequences, SEQ ID NOs, and corresponding CBP code names of exemplary peptides and peptidomimetics of the invention.

DETAILED DESCRIPTION OF THE INVENTION

The invention provides compounds, including peptides and peptidomimetics, that are useful for treating diseases characterized by an immune disorder, inflammatory response, and/or viral infection, including but not limited to, arthritis, auto-immune diseases, collagen diseases, allergy, asthma, pollinosis, atopy, or viral diseases. The invention further provides methods of using compounds of the invention to treat diseases characterized by an immune disorder, inflammatory response, and/or viral infection, including but not limited to, arthritis, auto-immune diseases, collagen diseases, allergy, asthma, pollinosis, atopy, or viral diseases.

The invention provides G2 cell cycle checkpoint-abrogating compounds that, surprisingly, have immune-modulating, anti-inflammatory, and anti-viral activity. G2 checkpoint-abrogating CBP compounds of the present invention are provided, in particular the CBP compounds disclosed in Table 3, wherein the CBP compounds have immune-modulating, anti-inflammatory, and anti-viral activity. In accordance with one aspect, methods are provided for treating diseases characterized by an immune disorder using CBP compounds of the present invention. In one embodiment, methods are provided for treating diseases characterized by an immune disorder using CBP501 (SEQ ID NO: 80). In accordance with another aspect, methods are provided for treating diseases characterized by an inflammatory response using CBP compounds of the present invention. In one embodiment, methods are provided for treating diseases characterized by an inflammatory response using compound CBP501 (SEQ ID NO: 80). In accordance with another aspect, method are provided for treating diseases characterized by a viral infection using CBP compounds of the present invention. In one embodiment, methods for inhibiting HIV replication are provided using compound CBP501 (SEQ ID NO:80).

Definitions

The following are abbreviations used herein:

Cha: cyclohexyl-alanine

Phe-2,3,4,5,6-F: Fluorine at positions 2,3,4,5, and 6 on phenyl residue of phenylalanine (Phe); PheF5

F: Fluorine

Bpa: Benzoyl-phenylalanine

Nal(2): 2-Naphthyl-alanyl
Ala(3-Bzt): (3-Benzothienyl)-alanine
Nal(1): 1-Naphthyl-alanyl
Dph: Diphenyl-alanine
Ala(tBu): t-Butyl-alanyl
Cys(tBu): t-Butyl-cysteine
Phe-3,4,5-F: Fluorines at position 3,4 and 5 on the phenyl of phenylalanine (Phe)
Phe-4CF$_3$: CF$_3$ at position 4 on the phenyl residue of phenylalanine (Phe)
Phe-3Br,4Cl,5Br: Bromine at position 3, chlorine at position 4, and bromine at position 5 on the phenyl of phenylalanine (Phe)
Phe-4Cl: Chlorine at position 4 on the phenyl of phenylalanine (Phe)
P1, P2, P3, P4, P5, P6, etc., or P7, P8, P9, P10, P11, P12, etc.: contiguous sequence of P1, P2, P3, P4, P5, P6, etc.; or P7, P8, P9, P10, P11, P12, respectively.
X1, X2, X3, X4, X5, X6, etc., or X7, X8, X9, X10, X11, X12, etc.: contiguous sequence of X1, X2, X3, X4, X5, X6, etc.; or X7, X8, X9, X10, X11, X12, respectively.

Unless otherwise defined, all technical or scientific terms used herein have the same meaning as commonly understood by one of ordinary skill in the art to which this invention belongs. Suitable methods and materials for practicing or testing the present invention are described herein; it is understood that methods or materials similar or equivalent to those described herein can be used to practice or test the present invention, All publications, patents or other references cited herein are incorporated by reference in their entirety. In case of conflict, the present specification, including definitions, will control.

As used herein, the singular forms "a", "or," "the" or "is" include plural referents unless the context clearly indicates otherwise. Thus, for example, reference to a "compound" includes a plurality of compounds or reference to "a residue" or an "amino acid" includes reference to one or more residues or amino acids.

"Disease" or "disorder" refers to an impairment of the normal function of an organism. As used herein, a disease may be characterized by, e.g., an immune disorder, an inflammatory response, viral infection, or a combination of any of these conditions.

"Immune-modulating" refers to the ability of a compound of the present invention to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

"Immune disorder" refers to abnormal functioning of the immune system. Immune disorders can be caused by deficient immune responses (e.g., HIV AIDS) or overactive immune responses (e.g., allergy, auto-immune disorders). Immune disorders can result in the uncontrolled proliferation of immune cells, uncontrolled response to foreign antigens or organisms leading to allergic or inflammatory diseases, aberrant immune responses directed against host cells leading to auto-immune organ damage and dysfunction, or generalized suppression of the immune response leading to severe and recurrent infections.

It is understood that "immune disorder" refers to disorders of the innate immune system (innate immunity) and the adaptive immune system (adaptive immunity). Innate immunity refers to an early system of defense that depends on invariant receptors recognizing common features of pathogens. The innate immune system provides barriers and mechanisms to inhibit foreign substances, in particular through the action of macrophages and neutrophils. The inflammatory response is considered part of innate immunity. The innate immune system is involved in initiating adaptive immune responses and removing pathogens that have been targeted by an adaptive immune response. However, innate immunity can be evaded or overcome by many pathogens, and does not lead to immunological memory.

Adaptive immunity refers to the ability to recognize pathogens specifically and to provide enhanced protection against reinfection due to immunological memory based on clonal selection of lymphocytes bearing antigen-specific receptors. A process of random recombination of variable receptor gene segments and the pairing of different variable chains generates a population of lymphocytes, each bearing a distinct receptor, forming a repertoire of receptors that can recognize virtually any antigen. If the receptor on a lymphocyte is specific for a ubiquitous self antigen, the cell is normally eliminated by encountering the antigen early in its development. Adaptive immunity is normally initiated when an innate immune response fails to eliminate a new infection, and antigen and activated antigen-presenting cells are delivered to draining lymphoid tissues. When a recirculating lymphocyte encounters its specific foreign antigen in peripheral lymphoid tissues, it is induced to proliferate and its progeny then differentiate into effector cells that can eliminate the infectious agent. A subset of these proliferating lymphocytes differentiate into memory cells, capable of responding rapidly to the same pathogen if it is encountered again.

Immune disorders caused by an impaired or immunocompromised immune system can produce a deficient immune response that leaves the body vulnerable to various viral, bacterial, or fungal opportunistic infections. Causes of immune deficiency can include various illnesses such as viruses, chronic illness, or immune system illnesses. Diseases characterized by an impaired immune system include, but are not limited to, HIV AIDS and severe combined immunodeficiency syndrome (SCIDS).

Immune disorders caused by an excessive response by the immune system. This excessive response can be an excessive response to one or more antigens on a pathogen, or to an antigen that would normally be ignored by the immune system. Diseases characterized by an overactive immune system include, but are not limited to, arthritis, allergy, asthma, pollinosis, atopy, and auto-immune diseases. Anaphylaxis is a term used to refer an excessive immune system response that can lead to shock.

"Arthritis" refers to inflammation of the joints that can be caused, inter alia, by wear and tear on joints, or auto-immune attack on connective tissues, or exposure to an allergen, e.g., as in adjuvant-induced arthritis. Arthritis is often associated with, or initiated by, deposition of antibody-antigen complexes in joint membranes and activation of an inflammatory response. Sometimes the immune response is initiated by cells rather than antibodies, where the cells can produce a deposit in the joint membrane.

"Allergy" refers to an immune reaction to a normally innocuous environmental antigen (allergen), resulting from the interaction of the antigen with antibodies or primed T cells generated by prior exposure to the same antigen. Allergy is characterized by immune and inflammatory aspects, as the allergic reaction is triggered by binding of the antigen to antigen-specific IgE antibodies bound to a high-affinity IgE receptor on mast cells, which leads to antigen-induced crosslinking of IgE on mast cell surfaces, causing the release of large amounts of inflammatory mediators such as histamine. Later events in the allergic response involve leukotrienes, cytokines, and chemokines, which recruit and activate eosinophils and basophils. The late phase of this response can evolve into chronic inflammation, characterized by the presence of effector T cells and eosinophils, which is most clearly seen in chronic allergic asthma.

"Asthma" refers to a chronic inflammatory disorder affecting the bronchial tubes, usually triggered or aggravated by allergens or contaminants. Asthma is characterized by constriction of the bronchial tubes, producing symptoms including, but not limited to, cough, shortness of breath, wheezing, excess production of mucus, and chest constriction "Atopy" refers to the tendency to develop so-called "classic" allergic diseases such as atopic dermatitis, allergic rhinitis (hay fever), and asthma, and is associated with a capacity to produce an immunoglobulin E (IgE) response to common allergens. Atopy is often characterized by skin allergies including but not limited to eczema, urticaria, and atopic dermatitis. Atopy can be caused or aggravated by inhaled allergens, food allergens, and skin contact with allergens, but an atopic allergic reaction may occur in areas of the body other than where contact with the allergan occurred. A strong genetic (inherited) component of atopy is suggested by the observation that the majority of atopic dermatitis patients have at least one relative who suffers from eczema, asthma, or hay fever. Atopy is sometimes called a "reagin response."

"Pollinosis," "hay fever," or "allergic rhinitis," are terms that refer to an allergy characterized by sneezing, itchy and watery eyes, a runny nose and a burning sensation of the palate and throat. Often seasonal, pollinosis is usually caused by allergies to airborne substances such as pollen, and the disease can sometimes be aggravated in an individual by exposure to other allergens to which the individual is allergic.

"Auto-immune" refers to an adaptive immune response directed at self antigens. "Auto-immune disease" refers to a condition wherein the immune system reacts to a "self" antigen that it would normally ignore, leading to destruction of normal body tissues. Auto-immune disorders are considered to be caused, at least in part, by a hypersensitivity reaction similar to allergies, because in both cases the immune system reacts to a substance that it normally would ignore. Auto-immune disorders include, but are not limited to, Hashimoto's thyroiditis, pernicious anemia, Addison's disease, type I (insulin dependent) diabetes, rheumatoid arthritis, systemic lupus erythematosus, dermatomyositis, Sjogren's syndrome, lupus erythematosus, multiple sclerosis, myasthenia gravis, Reiter's syndrome, and Grave's disease, alopecia areata, anklosing spondylitis, antiphospholipid syndrome, auto-immune hemolytic anemia, auto-immune hepatitis, auto-immune inner ear disease, auto-immune lymphoproliferative syndrome (ALPS), auto-immune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST syndrome, Crohn's disease, Dego's disease, dermatomyositis, dermatomyositis, discoid lupus, essential mixed cryoglobulinemia, fibromyalgia-fibromyositis, Guillain-Barre syndrome, idiopathic pulmonary fibrosis, idiopathic thrombocytopenia purpura (ITP), IgA nephropathy, juvenile arthritis, Meniere's disease, mixed connective tissue disease, pemphigus vulgaris, polyarteritis nodosa, polychondritis, polyglancular syndromes, polymyalgia rheumatica, polymyositis, primary agammaglobulinemia, primary biliary cirrhosis, psoriasis, Raynaud's phenomenon, rheumatic fever, sarcoidosis, scleroderma, stiff-man syndrome, Takayasu arteritis, temporal arteritis/giant cell arteritis, ulcerative colitis, uveitis, vasculitis, vitiligo, and Wegener's granulomatosis.

"Collagen disease," or "connective tissue disease," refers to a chronic inflammatory auto-immune disorder in which autoantibodies attack collagen found throughout the body. Connective tissues are composed of two major structural protein molecules, collagen and elastin; in collagen disease, autoantibodies directed against collagen will damage both collagen and elastin due to the resulting inflammation. Collagen diseases include, but are not limited to, lupus erythematosus, Sjogren's syndrome, scleroderma, dermatomyositis, and polyarteritis nodosa. Rheumatoid-collagen disease refers to a disorder affecting the connective tissue, with "rheumatic" symptoms including muscle stiffness, soreness and pain in the joints and associated structures.

"Inflammatory response" or "inflammation" is a general term for the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, auto-immune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion.

"Anti-inflammatory" refers to the ability of a compound of the present invention to prevent or reduce the inflammatory response, or to soothe inflammation by reducing the symptoms of inflammation such as redness, pain, heat, or swelling.

Inflammatory responses can be triggered by injury, for example injury to skin, muscle, tendons, or nerves. Inflammatory responses can also be triggered as part of an immune response. Inflammatory responses can also be triggered by infection, where pathogen recognition and tissue damage can initiate an inflammatory response at the site of infection. Generally, infectious agents induce inflammatory responses by activating innate immunity. Inflammation combats infection by delivering additional effector molecules and cells to augment the killing of invading microorganisms by the frontline macrophages, by providing a physical barrier preventing the spread of infection, and by promoting repair of injured tissue. "Inflammatory disorder" is sometimes used to refer to chronic inflammation due to any cause.

Diseases characterized by inflammation of the skin, often characterized by skin rashes, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis and roseacae.

Inflammation can result from physical injury to the skin resulting in the "wheal and flare reaction" characterized by a mark at the site of injury due to immediate vasodilatation, followed by an enlarging red halo (the flare) due to spreading vasodilation, and elevation of the skin (swelling, the wheal) produced by loss of fluid and plasma proteins from transiently permeable postcapillary venules at the site of injury.

Inflammation triggered by various kinds of injuries to muscles, tendons or nerves caused by repetitive movement of a part of the body are generally referred to as repetitive strain injury (RSI). Diseases characterized by inflammation triggered by RSI include, but are not limited to, bursitis, carpal tunnel syndrome, Dupuytren's contracture, epicondylitis (e.g. "tennis elbow"), "ganglion" (inflammation in a cyst that has formed in a tendon sheath, usually occurring on the wrist) rotator cuff syndrome, tendinitis (e.g., inflammation of the Achilles tendon), tenosynovitis, and "trigger finger" (inflammation of the tendon sheaths of fingers or thumb accompanied by tendon swelling).

It is understood that the terms "immune disorder" and "inflammatory response" are not exclusive. It is understood that many immune disorders include acute (short term) or chronic (long term) inflammation. It is also understood that inflammation can have immune aspects and non-immune aspects. The role(s) of immune and nonimmune cells in a particular inflammatory response may vary with the type of inflammatory response, and may vary during the course of an inflammatory response. Immune aspects of inflammation and diseases related to inflammation can involve both innate and adaptive immunity. Certain diseases related to inflammation represent an interplay of immune and nonimmune cell interactions, for example intestinal inflammation (Fiocchi et al., 1997, *Am J Physiol Gastrointest Liver Physiol* 273: G769-G775), pneumonia (lung inflammation), or glomerulonephritis.

It is further understood that many diseases are characterized by both an immune disorder and an inflammatory response, such that the use of discrete terms "immune disorder" or "inflammatory response" is not intended to limit the scope of use or activity of the compounds of the present invention with respect to treating a particular disease. For example, arthritis is considered an immune disorder characterized by inflammation of joints, but arthritis is likewise considered an inflammatory disorder characterized by immune attack on joint tissues. Thus, the observation that a compound of the invention, e.g., CBP501, reduces the inflammation seen in an animal model of arthritis, does not limit the observed activity of the compound to anti-inflammatory activity. In a disease having both immune and inflammatory aspects, merely measuring the effects of a compound of the present invention on inflammation does not exclude the possibility that the compound may also have immune-modulating activity in the same disease. Likewise, in a disease having both immune and inflammatory aspects, merely measuring the effects of a compound of the present invention on immune responses does not exclude the possibility that the compound may also have anti-inflammatory activity in the same disease.

"Viral infection" as used herein refers to infection of an organism by a virus that is pathogenic to that organism. It is understood that an infection is established after a virus has invaded tissues and then cells of the host organism, after which the virus has used the cellular machinery of the host to carry out functions that may include synthesis of viral enzymes, replication of viral nucleic acid, synthesis of viral packaging, and release of synthesized virus.

"Anti-viral" refers to the ability of a compound of the present invention to prevent, reduce, or eliminate a viral infection For example, an anti-viral compound of the invention may prevent viral attachment to cells, or viral entry, or viral uncoating, or synthesis of viral enzymes, or viral replication, or viral release. In particular, an anti-viral compound of the invention may prevent or otherwise inhibit viral replication in cells infected with the virus. An anti-viral compound of the invention may reduce (interfere with) viral attachment to cells, or viral entry, or viral uncoating, or synthesis of viral enzymes, or viral replication, or viral release, to such a degree that no significant disease (impairment of the normal function of an organism) results from the viral infection. An anti-viral compound of the invention may eliminate the viral infection by killing or weakening the virus so that it does not infect or replicate. An anti-viral compound of the invention may eliminate the viral infection through an immune-modulating effect that stimulates the immune system to kill the virus.

"Viral diseases," "diseases characterized by viral infection," and "diseases caused by viral infection" refer to impairment of the normal function of an organism as a result of viral infection. Diseases characterized by viral infection may include other aspects such as immune responses and inflammation. Compounds of the present invention are useful for treating diseases related to viral infection by RNA viruses, including retroviruses, or DNA viruses. A retrovirus includes any virus that expresses reverse transcriptase including, but not limited to, HIV-1, HIV-2, HTLV-I, HTLV-II, FeLV, FIV, SIV, AMV, MMTV, and MoMuLV.

Diseases related to viral infection can be caused by infection with a herpesvirus, arenavirus, coronavirus, enterovirus, bunyavirus, filovirus, flavivirus, hantavirus, rotavirus, arbovirus, Epstein-Barr virus, cytomegalovirus, infant cytomegalic virus, astrovirus, adenovirus and lentivirus, in particular HIV. Diseases related to viral infection (viral diseases) include, but are not limited to, molluscum contagiosum, HTLV, HTLV-1, HIV/AIDS, human papillomavirus, herpesvirus, herpes, genital herpes, viral dysentery, common cold, flu, measles, rubella, chicken pox, mumps, polio, rabies, mononucleosis, Ebola, respiratory syncytial virus (RSV), Dengue fever, yellow fever, Lassa fever, viral meningitis, West Nile fever, parainfluenza, chickenpox, smallpox, Dengue hemorrhagic fever, progressive multifocal leukoencephalopathy, viral gastroenteritis, acute Appendicitis, hepatitis A, hepatitis B, chronic hepatitis B, hepatitis C, chronic hepatitis C, hepatitis D, hepatitis E, hepatitis X, cold sores, ocular herpes, meningitis, encephalitis, shingles, pneumonia, encephalitis, California serogroup viral, St. Louis encephalitis, Rift Valley Fever, hand, foot, & mouth Disease, Hendra virus, Japanese encephalitis, lymphocytic choriomeningitis, roseola infantum, sandfly fever, SARS, warts, cat scratch disease, slap-cheek syndrome, orf, and pityriasis rosea.

It is understood that the terms "inflammatory response" and "viral infection" and "immune disorder" are not exclusive. Many diseases related to viral infection include inflammatory responses, where the inflammatory responses are usually part of the innate immune system triggered by the invading virus. Inflammation can also be triggered by physical (mechanical) injury to cells and tissues resulting from viral infection. Examples of viral infections characterized by inflammation include, but are not limited to: encephalitis, which is inflammation of the brain following viral infection with, e.g., arbovirus, herpesvirus, and measles (before vaccines were common); meningitis, which is inflammation of the meninges (the membranes that surround the brain and spinal cord) following infection; meningoencephalitis, which is infection and inflammation of both the brain and meninges; encephalomyelitis which is infection and inflammation of the brain and spinal cord; viral gastroenteritis, which is an inflammation of the stomach and intestines caused by a viral infection; viral hepatitis, which is an inflammation of the liver caused by viral infection.

As used herein, the terms "peptide," "polypeptide" and "protein" are used interchangeably and refer to two or more amino acids covalently linked by an amide bond or non-amide equivalent. The peptides of the invention can be of any length. For example, the peptides can have from about 5 to 100 or more residues, such as, 5 to 12, 12 to 15, 15 to 18, 18 to 25, 25 to 50, 50 to 75, 75 to 100, or more in length. The peptides of the invention include l- and d-isomers, and combinations of l- and d-isomers. The peptides can include modifications typically associated with post-translational processing of proteins, for example, cyclization (e.g., disulfide or amide bond), phosphorylation, glycosylation, carboxylation, ubiquitination, myristylation, or lipidation.

Peptides disclosed herein further include compounds having amino acid structural and functional analogues, for example, peptidomimetics having synthetic or non-natural amino acids or amino acid analogues, so long as the mimetic has one or more functions or activities of compounds of the invention, e.g., G2 checkpoint abrogating activity and detectable immune-modulating and/or anti-inflammatory and/or anti-viral activity. The compounds of the invention therefore include "mimetic" and "peptidomimetic" forms.

As used herein, the terms "mimetic" and "peptidomimetic" refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the mimetic's activity. As with polypeptides of the invention which are conservative variants, routine testing can be used to determine whether a mimetic has the requisite activity, e.g., G2 checkpoint abrogating activity and detectable immune-modulating and/or anti-inflammatory and/or anti-viral activity.

Peptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$^4$—), thiazole, retroamide, thioamide, or ester (see, e.g., Spatola (1983) in *Chemistry and Biochemistry of Amino Acids, Peptides and Proteins,* Vol. 7, pp 267-357, Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic rings include, for example, thiazolyl, thiophenyl, pyrazolyl, benzimidazolyl, naphthyl, furanyl, pyrrolyl, and pyridyl aromatic rings.

Mimetics of acidic amino acids can be generated by substitution with non-carboxylate amino acids while maintaining a negative charge; (phosphono) 8 alanine; and sulfated threonine. Carboxyl side groups (e.g., aspartyl or glutamyl) can also be selectively modified by reaction with carbodiimides (R'—N=C=N—R') including, for example, 1-cyclohexyl-3 (2-morpholinyl-(4-ethyl) carbodiimide or 1-ethyl-3 (4-azonia-4,4-dimetholpentyl) carbodiimide. Aspartyl or glutamyl groups can also be converted to asparaginyl and glutaminyl groups by reaction with ammonium ions.

Mimetics of basic amino acids can be generated by substitution, for example, in addition to lysine and arginine, with the amino acids ornithine, citrulline, or (guanidino)-acetic acid, or (guanidino)alkyl-acetic acid, where alkyl can be substituted or unsubstituted methyl, ethyl, propyl, hexyl, butyl, pentyl, isopropyl, iso-butyl, sec-isotyl, iso-pentyl, or a non-acidic amino acid. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine mimetics can be generated by reacting arginyl with one or more reagents including, for example, phenylglyoxal, 2,3-butanedione, 1,2-cyclohexanedione, or ninhydrin, optionally under alkaline conditions. Tyrosine residue mimetics can be generated by reacting tyrosyl with aromatic diazonium compounds or tetranitromethane. N-acetylimidizol and tetranitromethane can be used to form O-acetyl tyrosyl species and 3-nitro derivatives, respectively.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2, 4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, 3- or 4-hydroxy proline, dehydroproline, 3- or 4-methylproline, and 3,3,-dimethylproline. Histidine mimetics can be generated by reacting histidyl with diethylprocarbonate or para-bromophenacyl bromide. Other mimetics include, for example, those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

Invention peptides and peptidomimetics further include modified forms of the sequences set forth herein, provided that the modified form retains, at least a part of, the function of the unmodified or reference peptide or peptidomimetic. By way of an example, a modified peptide or peptidomimetic will retain detectable G2 checkpoint abrogating activity and activity against inflammation, arthritis, auto-immune diseases, collagen diseases, allergy, asthma, pollinosis or atopy although, relative to a reference peptide or peptidomimetic, it may have increased or decreased G2 abrogating activity or activity against inflammation, arthritis, auto-immune diseases, collagen diseases, allergy, asthma, pollinosis or atopy. By way of another example, a modified peptide or peptidomimetic will retain detectable G2 checkpoint abrogating activity and activity against viral infection, especially against HIV although, relative to a reference peptide or peptidomimetic, it may have increased or decreased G2 checkpoint abrogating activity and activity against viral infection, especially against HIV.

Modified peptides and peptidomimetics can have one or more amino acid residues substituted with another residue, or added to the sequence, or deleted from the sequence. In one embodiment, the modified peptide or peptidomimetic has one or more amino acid substitutions, additions or deletions (e.g., 1-3, 3-5, 5-10 or more). In one aspect, the substitution is with an amino acid or mimetic whose side chain occupies a similar space with the reference amino acid or mimetic (the amino acid or mimetic that is being substituted). In still another aspect, the substitution is with a non-human amino acid which is structurally similar to the human residue. In a particular aspect, the substitution is a conservative amino acid substitution.

As used herein, the term "similar space" means a chemical moiety that occupies a three-dimensional space similar in size to a reference moiety. Typically, a moiety that occupies a similar space will be similar in size to the reference moiety. An amino acid or mimetic that "occupies a similar side chain space" has a side chain that occupies a three-dimensional space similar in size to the reference amino acid or mimetic. Specific examples for d-(Phe-2,3,4,5,6-F), l-(Phe-2,3,4,5,6-F), d-(Phe-3,4,5F), l-(Phe-3,4,5F), d-(Phe-4CF3) or l-(Phe-4CF3), are (l or d-Phe-2R1,3R2,4R3,5R4,6R5) where R1,R2,R3,R4,R5 can be chloride, bromide, fluoride, iodide, hydrogen, hydrogen oxide or absent. For small molecules, e.g., fluoride which has a size of about 1 Angstrom, similar space may be absence of a moiety.

The term "conservative substitution" means the replacement of one amino acid by a biologically, chemically or structurally similar residue. Biologically similar means that the substitution is compatible with biological activity, e.g., G2 checkpoint abrogating activity and activity against inflammation, arthritis, auto-immune diseases, collagen diseases, allergy, asthma, pollinosis, atopy, or viral diseases, especially HIV. Structurally similar means that the amino acids have side chains with similar length, such as alanine, glycine and serine, or have similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Invention peptides and peptidomimetics therefore include peptides and peptidomimetics having a sequence that is not identical to peptide and peptidomimetic sequences set forth in Table 3. In one embodiment, a peptide or peptidomimetic has a sequence having 50%, 60%, 70%, 75%, 80%, 85%, 90%, 95%, or more identity with a sequence set forth in Table 3. In one aspect, the identity is over a defined area of the sequence, e.g., the amino or carboxy terminal 3-5 residues.

The compounds of the invention, including peptides and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga, A. K., *Therapeutic Peptides and Proteins, Formulation, Processing and Delivery Systems* (1995) Technomic Publishing Co., Lancaster, Pa.). Peptide synthesis can be performed using various solid phase techniques (see, e.g., Roberge (1995) *Science* 269:202; Merrifield (1997) *Methods Enzymol.* 289:3 13) and automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., *Organic Syntheses Collective Volumes,* Gilman, et al. (Eds) John Wiley & Sons, Inc., NY). Peptides and peptide mimetics can also be synthesized using combinatorial methodologies. Techniques for generating peptide and peptidomimetic libraries are well known, and include, for example, multipin, tea bag, and split couple mix techniques (ses, e.g., al-Obeidi (1998) *Mol. Biotechnol.* 9:205 223; Hruby (1997) *Curr. Opin. Chem. Biol.* 1:114 119; Ostergaard (1997) *Mol. Divers.* 3:17 27; and Ostresh (1996) *Methods Enzymol* 267:220 234). Modified peptides can be further produced by chemical modification methods (see, e.g., Belousov (1997) *Nucleic Acids Res.* 25:3440 3444; Frenkel (1995) *Free Radic. Biol. Med* 19:373 380; and Blommers (1994) *Biochemistry* 33:7886 7896).

Compounds of the Invention

In one embodiment, an invention compound comprises a contiguous peptide or peptidomimetic sequence that includes the following structure: P1, P2, P3, P4, P5, P6 (SEQ ID NO:1) or P6, P5, P4, P3, P2, P1 (SEQ ID NO:2); wherein P1 is d- or l-Cha, d- or l-Nal(2), d- or l-(Phe-2,3,4,5,6-F), d- or l-(Phe-3,4,5F), d- or l-(Phe-4CF$_3$), an amino acid that occupies a similar side chain space (e.g., d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group in the side chain; P2 is d- or l-Cha, d- or l-Nal(2), d- or l-(Phe-2,3,4,5,6-F), d- or l-(Phe-3,4,5F), d- or l-(Phe-4CF$_3$), d- or l-Bpa, d- or l-Phe4NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4; P6 is d- or l-Bpa, d- or l-Phe4NO$_2$, any amino acid and d- or l-Tyr (e.g., d-Ser-d-Tyr), any amino acid and d- or l-Phe (e.g., d-Ser-d-Phe), any amino acid, or nothing. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid, or a similar structure with one or more unsaturated carbon bonds.

In another embodiment, an invention compound comprises a contiguous peptide or peptidomimetic sequence that includes the following structure: P1, P2, P3, P4, P5, P6 (SEQ ID NO:3); P6, P5, P4, P3, P2, P1 (SEQ ID NO:4); P1, P2, P3, P4, P5, P6, P7, P8, P9, P10, P11, P12 (SEQ ID NO:5); P1, P2, P3, P4, P5, P6, P12, P11, P10, P9, P8, P7 (SEQ ID NO:6); P6, P5, P4, P3, P2, P1, P7, P8, P9, P10, P11, P12 (SEQ ID NO:7); P6, P5, P4, P3, P2, P1, P12, P11, P10, P9, P8, P7 (SEQ ID NO:8); P7, P8, P9, P10, P11, P12, P1, P2, P3, P4, P5, P6 (SEQ ID NO:9); P7, P8, P9, P10, P11, P12, P6, P5, P4, P3, P2, P1 (SEQ ID NO:10); P12, P11, P10, P9, P8, P7, P1, P2, P3, P4, P5, P6 (SEQ ID NO:11); P12, P11, P10, P9, P8, P7, P6, P5, P4, P3, P2, P1 (SEQ ID NO:12); P12, P11, P6, P9, P8, P7, P2, P1 (SEQ ID NO:13); P12, P11, P10, P6, P9, P4, P7, P2, P1 (SEQ ID NO:14); P1, P2, P7, P8, P9, P6, P11, P12 (SEQ ID NO:15); or P1, P2, P7, P4, P9, P6, P10, P11, P12 (SEQ ID NO:16); wherein P1 is d- or l-Cha, d- or l-Nal(2), d- or l-(Phe-2,3,4,5,6-F), d- or l-(Phe-3,4,5F), d- or l-(Phe-4CF$_3$), d- or l-Bpa, d- or l-Phe4NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF$_3$), or an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group(s) in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe4NO$_2$, any amino acid and d- or l-Tyr (e.g., d-Ser-d-Tyr), any amino acid and d- or l-Phe (e.g., d-Ser-d-Phe), and at least three of P7, P8, P9, P10, P11, P12 are basic amino acids with the rest being any amino acid or absent. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid or a a similar structure with one or more unsaturated carbon bonds.

In a further embodiment, an invention compound comprises a contiguous peptide or peptidomimetic sequence that includes the following structure: P1, P2, P3, P4, P5, P6, P7, P8, P9, P10, P11, P12 (SEQ ID NO:17); P12, P11, P10, P9, P8, P7, P6, P5, P4, P3, P2, P1 (SEQ ID NO:18); P12, P11, P10, P6, P9, P4, P7, P2, P1 (SEQ ID NO:19); or P1, P2, P7, P4, P9, P6, P10, P11, P12 (SEQ ID NO:20); wherein P1 is d- or l-Cha, d- or l-Nal(2), d- or l-(Phe-2,3,4,5,6-F), d- or l-(Phe-3,4,5F), d- or l-(Phe-4CF$_3$), d- or l-Bpa, d- or l-Phe4NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF$_3$), an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe4NO$_2$, any amino acid and d- or l-Tyr (e.g., d-Ser-d-Tyr), any amino acid and d- or l-Phe (e.g., d-Ser-d-Phe), any amino acid, or nothing; and at least three of P7, P8, P9, P10, P11, P12 are basic amino acids with the rest being any amino acid or absent. In various aspects, the amino acid having a simple carbon chain is d- or l-aminoundecanoic acid or d- or l-8-aminocaprylic acid.

In yet another embodiment, an invention compound comprises a contiguous peptide or peptidomimetic sequence that includes the following structure: P1, P2, P3, P4, P5, P6 (SEQ ID NO:21) or P6, P5, P4, P3, P2, P1 (SEQ ID NO:22); wherein P1 is d- or l-Cha, d- or l-Nal(2), d- or l-(Phe-2,3,4,5,6-F), d- or l-(Phe-3,4,5F), d- or l-(Phe-4CF$_3$), d- or l-Bpa, d- or l-Phe4NO$_2$, d- or l-Tyr, or d- or l-Phe; P2 is d- or l-Cha, d- or l-Nal(2), d- or l- (Phe-2,3,4,5,6-F), d- or l-(Phe-3,4,5F), d- or l-(Phe-4 CF$_3$), d- or l-Bpa, d- or l-Phe4NO$_2$, d- or l-Tyr, or d- or l-Phe; P3 is d- or l-serine, d- or l-arginine, d- or l-cysteine, d- or l-proline, or d- or l-asparagine; P4 is d- or l-tryptophan; and P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe4NO$_2$, (d-Ser-d-Tyr), or (d-Ser-d-Phe).

In still another embodiment, an invention compound comprises a contiguous peptide or peptidomimetic sequence that includes the following structure: P1, P2, P3, P4, P5, P6, P7, P8, P9, P10, P11, P12 (SEQ ID NO:23); P1, P2, P3, P4, P5, P6, P12, P11, P10, P9, P8, P7 (SEQ ID NO:24); P6, P5, P4, P3, P2, P1, P7, P8, P9, P10, P11, P12 (SEQ ID NO:25); P6, P5, P4, P3, P2, P1, P12, P11, P10, P9, P8, P7 (SEQ ID NO:26); P7, P8, P9, P10, P11, P12, P1, P2, P3, P4, P5, P6 (SEQ ID NO:27); P7, P8, P9, P10, P11, P12, P6, P5, P4, P3, P2, P1 (SEQ ID NO:28); P12, P11, P10, P9, P8, P7, P1, P2, P3, P4, P5, P6 (SEQ ID NO:29); P12, P11, P10, P9, P8, P7, P6, P5, P4, P3, P2, P1 (SEQ ID NO:30); P12, P11, P6, P9, P8, P7, P2, P1 (SEQ ID NO:31); P12, P11, P10, P6, P9, P4, P7, P2, P1 (SEQ ID NO:32); P1, P2, P7, P8, P9, P6, P11, P12 (SEQ ID NO:33); or P1, P2, P7, P4, P9, P6, P10, P11, P12 (SEQ ID NO:34); wherein P1 is d- or l-Cha, Nal(2), d- or l-(Phe-2,3,4,5,6-F), d- or l-(Phe-3,4,5F), d- or l-(Phe-4 CF$_3$), d- or l-Bpa, d- or l-Phe4NO$_2$, d- or l-Tyr, or d- or l-Phe; P2 is d- or l-Cha, d- or l-Nal(2), d- or l-(Phe-2,3,4,5,6-F), d- or l-(Phe-3,4,5F), d- or l-(Phe-4 CF$_3$), d- or l-Bpa, d- or l-Phe4NO$_2$, d- or l-Tyr, or d- or l-Phe; P3 is d- or l-serine, d- or l-arginine, d- or l-cysteine, d- or l-proline, or d- or l-asparagine; P4 is d- or l-tryptophan; P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe4NO$_2$, (d-Ser-d-Tyr), or (d-Ser-d-Phe); and at least three of P7, P8, P9, P10, P11, P12 are d- or l-Arg or d- or l-Lys with the rest being any amino acid or absent.

In an additional embodiment, an invention compound comprises a contiguous peptide or peptidomimetic sequence that includes the following structure: P1, P2, P3, P4, P5, P6, P7, P8, P9, P10, P11, P12 (SEQ ID NO:35); P12, P11, P10, P9, P8, P7, P6, P5, P4, P3, P2, P1 (SEQ ID NO:36); P12, P11, P10, P6, P9, P4, P7, P2, P1(SEQ ID NO:37); or P1, P2, P7, P4, P9, P6, P10, P11, P12 (SEQ ID NO:38); wherein P1 is d- or l-Cha, or d- or l-Nal(2); P2 is d- or l-(Phe-2,3,4,5,6-F), d- or l-(Phe-3,4,5F), d- or l-(Phe-4 $CF_3$); and at least three of P7, P8, P9, P10, P11, P12 are d- or l-Arg with the rest being any amino acid or absent; P3 is d- or l-serine; P4 is d- or l-tryptophan; P5 is d- or l-serine or d- or l-asparagine; P6 is d- or l-Bpa, d- or l-Phe4$NO_2$, (d- or l-Ser-d- or l-Tyr), or (d- or l-Ser-d- or l-Phe).

In yet an additional embodiment, an invention compound comprises a contiguous peptide or peptidomimetic sequence that includes the following structure: P1, P2, P3, P4, P5, P6 (SEQ ID NO:39) or P6, P5, P4, P3, P2, P1 (SEQ ID NO:40); wherein P1 is d- or l-Cha, or d- or l-Nal(2); P2 is (d- or l-Phe-2,3,4,5,6-F), (d- or l-Phe-3,4,5F) or (d- or l-Phe-4$CF_3$); P3 is d- or l-Ser; P4 is d- or l-Trp; P5 is d- or l-Ser; P6 is d- or l-Bpa, or (d- or l-Ser-d- or l-Tyr).

In a further embodiment, an invention compound comprises a contiguous peptide or peptidomimetic sequence that includes the following structure: P1, P2, P3, P4, P5, P6 (SEQ ID NO:41); P6, P5, P4, P3, P2, P1 (SEQ ID NO:42); P1, P2, P3, P4, P5, P6, P7, P8, P9, P10, P11, P12 (SEQ ID NO:43); P1, P2, P3, P4, P5, P6, P12, P11, P10, P9, P8, P7 (SEQ ID NO:44); P6, P5, P4, P3, P2, P1, P7, P8, P9, P10, P11, P12 (SEQ ID NO:45); P6, P5, P4, P3, P2, P1, P12, P11, P10, P9, P8, P7 (SEQ ID NO:46); P7, P8, P9, P10, P1, P12, P1, P2, P3, P4, P5, P6 (SEQ ID NO:47); P7, P8, P9, P10, P11, P12, P6, P5, P4, P3, P2, P1 (SEQ ID NO:48); P12, P11, P10, P9, P8, P7, P1, P2, P3, P4, P5, P6 (SEQ ID NO:49); P12, P11, P10, P9, P8, P7, P6, P5, P4, P3, P2, P1 (SEQ ID NO:50); P12, P11, P6, P9, P8, P7, P2, P1 (SEQ ID NO:51); P12, P11, P10, P6, P9, P4, P7, P2, P1 (SEQ ID NO:52); P1, P2, P7, P8, P9, P6, P11, P12 (SEQ ID NO:53); or P1, P2, P7, P4, P9, P6, P10, P11, P12 (SEQ ID NO:54); wherein P1 is d- or l-Cha, or d- or l-Nal(2); P2 is (d- or l-Phe-2,3,4,5,6-F), (d- or l-Phe-3,4,5F) or (d- or l-Phe-4$CF_3$); P3 is any amino acid (e.g., d- or l-Ser, or d- or l-Pro); P4 is d- or l-Trp; P5 is any amino acid (e.g., d- or l-Ser); P7 is d- or l-Arg; P8 is d- or l-Arg; P9 is d- or l-Arg; P10 is d- or l-Gln or d- or l-Arg; P1 is d- or l-Arg; P12 is d- or l-Arg; P6 is d- or l-Bpa or (d- or l-Ser-d- or l-Tyr).

In still another embodiment, an invention compound comprises a contiguous peptide or peptidomimetic sequence that includes the following structure: P1, P2, P3, P4, P5, P6, P7, P8, P9, P10, P11, P12 (SEQ ID NO:55); P12, P11, P10, P9, P8, P7, P6, P5, P4, P3, P2, P1 (SEQ ID NO:56); P12, P11, P10, P6, P9, P4, P7, P2, P1 (SEQ ID NO:57); or P1, P2, P7, P4, P9, P6, P10, P11, P12 (SEQ ID NO:58); wherein P1 is d- or l-Cha or d- or l-Nal(2); P2 is (d- or l-Phe-2,3,4,5,6-F); P3 is d- or l-Ser; P4 is d- or l-Trp; P5 is d- or l-Ser; P7 is d- or l-Arg; P8 is d- or l-Arg; P9 is d- or l-Arg; P10 is d- or l-Gln or d- or l-Arg; P11 is d- or l-Arg; P12 is d- or l-Arg; P6 is d- or l-Bpa or (d- or l-Ser-d- or l-Tyr).

In still further embodiments, an invention compound comprises a contiguous peptide or peptidomimetic sequence that includes the following structure: (d-Bpa) (d-Ser)(d-Trp)(d-Ser) (d-Phe-2,3,4,5,6-F) (d-Cha)(d-Arg) (d-Arg) (d-Arg) (d-Gln)(d-Arg) (SEQ ID NO:99) (d-Arg) (d-Arg) (d-Arg) (d-Gln)(d-Arg) (d-Arg) (d-Bpa)(d-Ser)(d-Trp)(d-Ser) (d-Phe-2,3,4,5,6-F) (d-Cha) (SEQ ID NO:100); (d-Bpa) (d-Ser)(d-Trp)(d-Ser) (d-Phe-2,3,4,5,6-F)(d-Cha)(d-Arg) (d-Arg) (d-Gln) (d-Arg) (d-Arg) (d-Arg) (SEQ ID NO:59); (d-Arg) (d-Arg) (d-Gln) (d-Arg) (d-Arg) (d-Arg) (d-Bpa) (d-Ser)(d-Trp)(d-Ser) (d-Phe-2,3,4,5,6-F) (d-Cha) (SEQ ID NO:60); (d-Cha) (d-Phe-2,3,4,5,6-F) (d-Ser)(d-Trp)(d-Ser) (d-Bpa) (d-Arg) (d-Arg) (d-Arg) (d-Gln)(d-Arg) (d-Arg) (SEQ ID NO:61); (d-Arg) (d-Arg) (d-Arg) (d-Gln)(d-Arg) (d-Arg) (d-Cha) (d-Phe-2,3,4,5,6-F) (d-Ser)(d-Trp)(d-Ser) (d-Bpa) (SEQ ID NO:62); (d-Cha) (d-Phe-2,3,4,5,6-F) (d-Ser) (d-Trp) (d-Ser) (d-Bpa) (d-Arg) (d-Arg) (d-Gln) (d-Arg) (d-Arg) (d-Arg) (SEQ ID NO:63); (d-Arg) (d-Arg) (d-Gln) (d-Arg) (d-Arg) (d-Arg) (d-Cha) (d-Phe-2,3,4,5,6-F) (d-Ser)(d-Trp)(d-Ser) (d-Bpa) (SEQ ID NO:64); (d-Arg) (d-Arg) (d-Arg) (d-Arg) (d-Arg) (d-Cha) (d-Phe-2,3,4,5,6-F) (d-Ser) (d-Trp)(d-Ser) (d-Bpa) (SEQ ID NO:65); (d-Cha) (d-Phe-2,3,4,5,6-F) (d-Ser)(d-Trp)(d-Ser) (d-Bpa) (d-Arg) (d-Arg) (d-Arg) (d-Arg) (d-Arg) (d-Arg) (SEQ ID NO:66); (d-Arg) (d-Arg) (d-Arg) (d-Arg) (d-Arg) (d-Arg) (d-Bpa) (d-Ser)(d-Trp)(d-Ser) (d-Phe-2,3,4,5,6-F)(d-Cha) (SEQ ID NO:67); (d-Bpa) (d-Ser)(d-Trp)(d-Ser) (d-Phe-2,3,4,5,6-F)(d-Cha) (d-Arg) (d-Arg) (d-Arg) (d-Arg) (d-Arg) (d-Arg) (SEQ ID NO:68); (d-Arg)(d-Arg)(d-Bpa) (d-Arg) (d-Arg) (d-Arg) (d-Phe-2,3,4,5,6-F)(d-Cha) (SEQ ID NO:69); (d-Cha) (d-Phe-2,3,4,5,6-F) (d-Arg) (d-Arg) (d-Arg) (d-Bpa) (d-Arg)(d-Arg) (d-Arg) (SEQ ID NO:70); (d-Arg) (d-Arg) (d-Bpa) (d-Arg)(d-Trp) (d-Arg) (d-Phe-2,3,4,5,6-F)(d-Cha) (SEQ ID NO:71); (d-Cha) (d-Phe-2,3,4,5,6-F) (d-Arg)(d-Trp) (d-Arg) (d-Bpa) (d-Arg) (d-Arg) (d-Arg) (SEQ ID NO:72); (d-Arg) (d-Arg) (d-Arg) (d-Arg) (d-Bpa) (d-Arg)(d-Trp) (d-Arg) (d-Phe-2,3,4,5,6-F)(d-Cha) (SEQ ID NO:73); (d-Cha) (d-Phe-2,3,4,5,6-F) (d-Arg)(d-Trp) (d-Arg) (d-Bpa) (d-Arg) (d-Arg) (d-Arg) (d-Arg) (SEQ ID NO:74); (d-Arg) (d-Arg)(d-Arg)(d-Bpa)(d-Arg)(d-Arg) (d-Arg) (d-Phe-2,3,4,5,6-F)(d-Cha) (SEQ ID NO:75); or (d-Cha) (d-Phe-2,3,4,5,6-F) (d-Arg) (d-Arg) (d-Arg) (d-Bpa) (d-Arg) (d-Arg)(d-Arg) (SEQ ID NO:76).

In still additional embodiments, an invention compound comprises a contiguous peptide or peptidomimetic sequence that includes the following structure: (d-Bpa)(d-Ser)(d-Trp) (d-Ser)(d-Phe-2,3,4,5,6-F)(d-Cha)(d-Arg)(d-Arg)(d-Arg)(d-Gln)(d-Arg)(d-Arg) (SEQ ID NO:77).

In further embodiments, an invention compound comprises a contiguous peptide or peptidomimetic sequence: $X_1$ $X_2 X_3 X_4 X_5 X_6 X_7 X_8 X_9 X_{10} X_{11}$ (SEQ ID NO:137), wherein $X_1$ is L, F, W, M, R, I, V, Y, K, or absent, $X_2$ is Y, F, A, W, S or T, $X_3$ is any amino acid, $X_4$ is any amino acid, $X_5$ is any amino acid, $X_6$ is S, A, N, H or P, $X_7$ is any amino acid, $X_8$ is any amino acid, $X_9$ is any amino acid or absent, $X_{10}$ is N, G, L, S, M, P, N, A or absent, and $X_{11}$ is L or absent. In various aspects, $X_1$ is L, F, W, M, R or absent or $X_1$ is L, F or W; $X_2$ is Y, F, A; $X_3$ is R, T, S, H, D, G, A, L, K, A, N, Q or P, or $X_3$ is R, T, S, H, D, G, A or L, or $X_3$ is R, T, S or H; $X_4$ is S, T, G, A, L, R, I, M, V, P, or $X_4$ is S, T, G, A, L, R, or $X_4$ is S; $X_5$ is P, A, G, S or T, or $X_5$ is P; $X_6$ is S, N, H, P, A, G or T, or $X_6$ is S, N or H, or $X_6$ is S; $X_7$ is M, F, Y, D, E, N, Q, H, G, I, L, V, A, P, N or W, or $X_7$ is M, F, Y, D, E, N, Q or H, or $X_7$ is M, F, Y, Q or H; $X_8$ is P, F, Y, W, L, G, M, D, E, N, Q, H, I, V, A or P, or $X_8$ is P, F, Y or W, or $X_8$ is Y; $X_9$ is E, G, L, S, M, P, N, D, A, T, P or absent; $X_{10}$ is absent; $X_{11}$ is absent. In still further embodiments, $X_2$ is Y, $X_5$ is P, and $X_{10}$ is N; $X_3$ is R, $X_8$ is P, and $X_{11}$ is L; and $X_4$ is S, $X_5$ is P, $X_6$ is S, $X_9$ is E, $X_{10}$ is N and $X_{11}$ is L.

In further embodiments, an invention compound comprises a contiguous peptide or peptidomimetic sequence: Y G G P G G G N (SEQ ID NO:138); R Y S L P P E L S N M (SEQ ID NO:139); L A R S A S M P E A L (SEQ ID NO:140); L Y R S P S M P E N L (SEQ ID NO:141); L Y R S P A M P E N L (SEQ ID NO:142); W Y R S P S F Y E N L (SEQ ID NO:143); W Y R S P S Y Y E N L (SEQ ID NO:144); or, W Y R S P S Y Y (SEQ ID NO:145).

In alternative embodiments, an invention compound comprises a contiguous peptide or peptidomimetic sequence: L Y R S P S Y P E N L (SEQ ID NO:146); L Y R S P S Y F E N L (SEQ ID NO:147); L Y R S P S Y Y E N L (SEQ ID NO:148); L Y R S P S Y W E N L (SEQ ID NO:149); L Y R S P S N P E N L (SEQ ID NO:150); L Y R S P S N F E N L (SEQ ID NO:151); L Y R S P S N Y E N L (SEQ ID NO:152); L Y R S P S N W E N L (SEQ ID NO:153); L Y R S P S H P E N L (SEQ ID NO:154); L Y R S P S H F E N L (SEQ ID NO:155); L Y R S P S H Y E N L (SEQ ID NO:156); L Y R S P S H W E N L (SEQ ID NO:157); L Y S S P S M P E N L (SEQ ID NO:158); L Y S S P S M F E N L (SEQ ID NO:159); L Y S S P S M Y E N L (SEQ ID NO:160); L Y S S P S M W E N L (SEQ ID NO:161); L Y S S P S F P E N L (SEQ ID NO:162); L Y S S P S F P E N L (SEQ ID NO:163); L Y S S P S F F E N L (SEQ ID NO:164); L Y S S P S F Y E N L (SEQ ID NO:165); L Y S S P S F W E N L (SEQ ID NO:166); L Y S S P S Y P E N L (SEQ ID NO:167); L Y S S P S Y F E N L (SEQ ID NO:168); L Y S S P S Y Y E N L (SEQ ID NO:169); L Y S S P S Y W E N L (SEQ ID NO:170); L Y S S P S Q P E N L (SEQ ID NO:171); L Y S S P S Q W E N L (SEQ ID NO:172); L Y S S P S H P E N L (SEQ ID NO:173); L Y S S P S H F E N L (SEQ ID NO:174); L Y S S P S H Y E N L (SEQ ID NO:175); L Y S S P S H W E N L (SEQ ID NO:176); L Y T S P S M P E N L (SEQ ID NO:177); L Y T S P S M F E N L (SEQ ID NO:178); L Y T S P S M Y E N L (SEQ ID NO:179); L Y T S P S M W E N L (SEQ ID NO:180); L Y T S P S F P E N L (SEQ ID NO:181); L Y T S P S F F E N L (SEQ ID NO:182); L Y T S P S F Y E N L (SEQ ID NO:183); L Y T S P S F W E N L (SEQ ID NO:184); L Y T S P S Y P E N L (SEQ ID NO:185); L Y T S P S Y F E N L (SEQ ID NO:186); L Y T S P S Y Y E N L (SEQ ID NO:187); L Y T S P S Y W E N L (SEQ ID NO:188); L Y T S P S N P E N L (SEQ ID NO:189); L Y T S P S N F E N L (SEQ ID NO:190); L Y T S P S N Y E N L (SEQ ID NO:191); L Y T S P S N W E N L (SEQ ID NO:192); L Y T S P S H P E N L (SEQ ID NO:193); L Y T S P S H F E N L (SEQ ID NO:194); L Y T S P S H Y E N L (SEQ ID NO:195); L Y T S P S H W E N L (SEQ ID NO:196); L Y H S P S Y P E N L (SEQ ID NO:197); L Y H S P S Y F E N L (SEQ ID NO:198); L Y H S P S Y Y E N L (SEQ ID NO:199); L Y H S P S Y W E N L (SEQ ID NO:200); L F T S P S Y P E N L (SEQ ID NO:201); L F T S P S Y F E N L (SEQ ID NO:202); L F T S P S Y Y E N L (SEQ ID NO:203); L F T S P S Y W E N L (SEQ ID NO:204); F Y S S P S H P E N L (SEQ ID NO:205); F Y S S P S H F E N L (SEQ ID NO:206); F Y S S P S H Y E N L (SEQ ID NO:207); F Y S S P S H W E N L (SEQ ID NO:208); F Y T S P S M P E N L (SEQ ID NO:209); F Y T S P S M F E N L (SEQ ID NO:210); F Y T S P S M Y E N L (SEQ ID NO:211); F Y T S P S M W E N L (SEQ ID NO:212); F Y T S P S F P E N L (SEQ ID NO:213); F Y T S P S F F E N L (SEQ ID NO:214); F Y T S P S F Y E N L (SEQ ID NO:215); F Y T S P S F W E N L (SEQ ID NO:216); F Y T S P S Y P E N L (SEQ ID NO:217); F Y T S P S Y F E N L (SEQ ID NO:218); F Y T S P S Y Y E N L (SEQ ID NO:219); F Y T S P S Y W E N L (SEQ ID NO:220); W Y R S P S M P E N L (SEQ ID NO:221); W Y R S P S M F E N L (SEQ ID NO:222); W Y R S P S M Y E N L (SEQ ID NO:223); W Y R S P S M W E N L (SEQ ID NO:224); W Y R S P S F P E N L (SEQ ID NO:225); W Y R S P S F F E N L (SEQ ID NO:226); W Y R S P S F Y E N L (SEQ ID NO:227); W Y R S P S F W E N L (SEQ ID NO:228); W Y R S P S Y P E N L (SEQ ID NO:229); W Y R S P S Y F E N L (SEQ ID NO:230); W Y R S P S Y Y E N L (SEQ ID NO:231); W Y R S P S Y W E N L (SEQ ID NO:232); W Y T S P S M P E N L (SEQ ID NO:233); W Y T S P S M F E N L (SEQ ID NO:234); W Y T S P S M Y E N L (SEQ ID NO:235); W Y T S P S M W E N L (SEQ ID NO:236); W Y T S P S F P E N L (SEQ ID NO:237); W Y T S P S F F E N L (SEQ ID NO:238); W Y T S P S F Y E N L (SEQ ID NO:239); W Y T S P S F W E N L (SEQ ID NO:240); W Y T S P S Y P E N L (SEQ ID NO:241); W Y T S P S Y F E N L (SEQ ID NO:242); W Y T S P S Y Y E N L (SEQ ID NO:243); W Y T S P S Y W E N L (SEQ ID NO:244); W Y T S P S H P E N L (SEQ ID NO:245); W Y T S P S H F E N L (SEQ ID NO:246); W Y T S P S H Y E N L (SEQ ID NO:247); W Y T S P S H W E N L (SEQ ID NO:248); L K R S P S M P E N L (SEQ ID NO:249); L Y I S P S M P E N L (SEQ ID NO:250) or L Y R S P S M V E N L (SEQ ID NO:251).

Invention compounds optionally include a cell membrane permeant sequence to assist in traversing the cell membrane. The cell membrane permeant sequence can comprise a polypeptide, such as a TAT protein transduction domain, e.g., a sequence Y G R K K R R Q R R R (SEQ ID NO:252). Invention compounds optionally contain a poly-lys and/or arg sequence in order to assist traversing the cell membrane. In certain embodiments, the invention compounds do not have a poly-lys and/or arg sequence that assists with cell entry. Exemplary embodiments of minimum sequence without a poly-lys/arg sequence assisting with cell membrane traversal include, but are not limited to: P6, P5, P4, P3, P2, P1 e.g., d-Bpa, d-Ser, d-Trp, d-Ser, d-Phe-2,3,4,5,6F, d-Cha (SEQ ID NO:101); d-Tyr, d-Ser, d-Pro, d-Trp, d-Ser, d-Phe-2,3,4,5,6F, d-Cha (SEQ ID NO:102); d-Bpa, d-Cys, d-Trp, d-Ser, d-Phe-2,3,4,5,6F, d-Cha, d-Cys (SEQ ID NO:103); and d-Tyr, d-Cys, d-Pro, d-Trp, d-Ser, d-Phe-2,3,4,5,6F, d-Cha, d-Cys (SEQ ID NO:104). In certain embodiments, the Cys residues are optionally cyclized.

CBP Compounds Having Immune-modulating and/or Anti-inflammatory and/or Anti-viral Activity.

In accordance with one aspect of the invention, CBP compounds with immune-modulating and/or anti-inflammatory activity and/or anti-viral activity are provided herein. It is known that CBP G2 checkpoint-abrogating compounds inhibit kinases and/or 14-3-3 proteins, and it is further known that kinases and 14-3-3 proteins are involved in certain signal transduction pathways. Surprisingly, as disclosed herein, CBP compounds with G2-checkpoint-abrogating activity also have immune-modulating and/or anti-inflammatory and/ or anti-viral activity. CBP compounds with immune-modulating and/or anti-inflammatory activity and/or anti-viral activity in accordance with the present invention include, but are not limited to the following CBP compounds: CBP413 (SEQ ID NO: 105); CBP420 (SEQ ID NO: 106); CBP430 (SEQ ID NO: 107); CBP431 (SEQ ID NO: 108); CBP432 (SEQ ID NO: 109); CBP440 (SEQ ID NO: 110); CBP450 (SEQ ID NO: 111); CBP451 (SEQ ID NO: 87); CBP452 (SEQ ID NO: 88); CBP454 (SEQ ID NO: 112); CBP455 (SEQ ID NO: 113); CBP460 (SEQ ID NO: 114); CBP461 (SEQ ID NO: 115); CBP462 (SEQ ID NO: 116); CBP463 (SEQ ID NO: 117); CBP464 (SEQ ID NO: 118); CBP465 (SEQ ID NO: 119); CBP466 (SEQ ID NO: 120); CBP470 (SEQ ID NO: 121); CBP471 (SEQ ID NO: 122); CBP481 (SEQ ID NO: 123); CBP500 (SEQ ID NO: 124); CBP501 (SEQ ID NO: 80); CBP502 (SEQ ID NO: 125); CBP503 (SEQ ID NO: 126); CBP504 (SEQ ID NO: 127); CBP505 (SEQ ID NO: 128); CBP506 (SEQ ID NO: 129); CBP510 (SEQ ID NO: 93); CBP511 (SEQ ID NO: 94); CBP512 (SEQ ID NO: 95); CBP601 (SEQ ID NO: 130); CBP602 (SEQ ID NO: 131); CBP603 (SEQ ID NO: 89); CBP604 (SEQ ID NO: 132); CBP605 (SEQ ID NO: 133); CBP606 (SEQ ID NO: 134); CBP607 (SEQ ID NO: 90); CBP608 (SEQ ID NO: 91);

CBP609 (SEQ ID NO: 92); CBP700 (SEQ ID NO: 96); CBP701 (SEQ ID NO: 97); CBP702 (SEQ ID NO: 98); CBP703 (SEQ ID NO: 99); CBP524 (SEQ ID NO: 135); and CBP721 (SEQ ID NO: 136). The sequence of each of the preceding CBP compounds is disclosed in Table 3

In accordance with a particular aspect of the invention, G2-checkpoint-abrogating CBP compounds with immune-modulating and/or anti-inflammatory activity and/or anti-viral activity include regions A and B arranged to form any of the following structures: P1,P2,P3,P4,P5 P6,P7,P8,P9,P10, P11 (SEQ ID NO: 253) or P6,P7,P8,P9,P10, P11,P1,P2,P3, P4,P5 (SEQ ID NO: 254), or P1,P2,P3,P4,P5 (SEQ ID NO: 255) where P1 and P5 are Bpa, or Tyr, or Phe, or (Cha)(Phe-2,3,4,5,6-F), or TyrTyr, or PhePhe, or a moiety that occupies a similar side chain space as that occupied by one or two benzene-like or cyclohexane-like side chain structures, where the moiety can be one or two amino acids or amino acid structural/functional analogues, including non-natural amino acids, synthetic amino acids, amino acid mimetics, and chimeric molecules. Positions P2 and P4 are any amino acid, and P3 is Trp or any moeity that occupies a similar side chain space as that occupied by the Trp side chain. Positions P6, P7, P8, P9, P10, P11 include Arg at five or more positions when P2 and/or P3 are not Arg, and any non-Arg position can be any amino acid or nothing. When P2 and/or P3 are Arg, then P6-P 11 can contain fewer than five Arg. The invention provides CBP compounds having the P1,P2,P3,P4,P5 P6,P7,P8,P9, P10,P11 (SEQ ID NO: 253) or P6,P7,P8,P9,P10,P11,P1,P2, P3,P4,P5 (SEQ ID NO: 254) structure described above, and having G2 checkpoint abrogating activity similar to that of compound CBP501 (SEQ ID NO: 80), wherein these CBP compounds include, but are not limited to: CBP500 (SEQ ID NO: 124); CBP501 (SEQ ID NO: 80); CBP504(SEQ ID NO: 127); CBP505 (SEQ ID NO: 128); CBP506 (SEQ ID NO: 129); CBP510 (SEQ ID NO: 93); CBP511 (SEQ ID NO: 94); CBP512 (SEQ ID NO: 95); CBP603 (SEQ ID NO: 89). Accordingly, CBP compounds with immune-modulating and/or anti-inflammatory activity and/or anti-viral activity as provided herein include but are not limited to: CBP500 (SEQ ID NO: 124); CBP501 (SEQ ID NO: 80); CBP504 (SEQ ID NO: 127); CBP505 (SEQ ID NO: 128); CBP506 (SEQ ID NO: 129); CBP510 (SEQ ID NO: 93); CBP511 (SEQ ID NO: 94); CBP512 (SEQ ID NO: 95); CBP603 (SEQ ID NO: 89).

In accordance with another aspect of the invention, P6-P11 is not required when another way of introducing CBP compounds into cells is provided, e.g., when CBP compounds are introduced into cells by a lipsomal carrier. Accordingly, the invention provides compounds having the structure P1,P2,P3, P4,P5 (SEQ ID NO: 255) where P1 and P5 are Bpa, or Tyr, or Phe, or (Cha)(Phe-2,3,4,5,6-F), or TyrTyr, or PhePhe, or a moiety that occupies a similar side chain space as that occupied by one or two benzene-like or cyclohexane-like side chain structures, where the moiety can be one or two amino acids or amino acid structural/functional analogues, including non-natural amino acids, synthetic amino acids, amino acid mimetics, and chimeric molecules. Positions P2 and P4 are any amino acid, and P3 is Trp or any moeity that occupies a similar side chain space as that occupied by the Trp side chain.

Compound CBP501 Having Immune-modulating and Anti-inflammatory Activity.

In one embodiment, CBP501 (SEQ ID NO: 80) is an immune-modulating and/or anti-inflammatory compound as provided herein. The amino acid sequence of CBP501 (SEQ ID NO:80) is disclosed in Table 3. The cell cycle G2 checkpoint abrogating peptide CBP501 was developed as disclosed in U.S. application Ser. No. 10/347,145, using a phenotype-based screening that efficiently identifies compounds having selective G2 checkpoint abrogation activity. As previously disclosed in U.S. application Ser. No. 10/347,145, CBP501 inhibits the phosphorylation activities of variety of kinases involved in the cell cycle G2 checkpoint, including mitogen activated kinase p38, and CBP501 binds 14-3-3 protein. In the present invention as disclosed herein, CBP501 was tested for its effects on diseases characterized by an immune disorder or inflammatory response, and results from animal models of allergy and arthritis demonstrated that CBP501 has immune-modulating and anti-inflammatory activity.

In one embodiment, CBP501 has anti-allergic activity and can be used to treat allergic disorders. As shown in Example 1 and Table 1 infra, CBP501 was found to have anti-allergic activity in a model of passive cutaneous anaphylaxis (PCA) in rats, where intraperitoneal administration of CBP501 at 20, 10 and 5 mg/kg inhibited allergic reactions by 93%, 93% and 87%, respectively. The effectiveness of CBP501 was equal to or greater than that of the antihistamine cyproheptadine-HCl in the same experimental system.

As shown in Example 2 and Table 2 infra, CBP501 was found to have anti-inflammatory activity in adjuvant-induced arthritis in rats, wherein intraperitoneal administration of 10 mg/kg as a single dose, or 5 mg/kg once daily for 5 consecutive days, produced significant anti-inflammatory activity in both acute and late phase of adjuvant-induced arthritis. The effectiveness of CBP501 was equal to or greater than that of hydrocortisone (30 mg/kg daily for 5 days) in the same experimental system.

CBP Compounds CBP500, CBP504, CBP505, CBP506, CBP510, CBP511, CBP512, and CBP603 Having Immune-modulating and/or Anti-inflammatory Activity.

CBP compounds having G2 checkpoint abrogating activity similar to that of peptide CBP501 (SEQ ID NO: 80) include, but are not limited to, CBP500 (SEQ ID NO: 124), CBP 504 (SEQ ID NO: 127), CBP 505 (SEQ ID NO: 128), CBP 506 (SEQ ID NO: 129), CBP 510 (SEQ ID NO: 93), CBP 511 (SEQ ID NO: 94), CBP 512 (SEQ ID NO: 95), and CBP 603 (SEQ ID NO: 89). The sequences of all of the preceding CBP compounds are disclosed in table 3. In one embodiment, CBP 500 (SEQ ID NO: 124) is an immune-modulating and/or anti-inflammatory compound useful for treating diseases characterized by an immune disorder or inflammatory response. In another embodiment, CBP 504 (SEQ ID NO: 127) is an immune-modulating and/or anti-inflammatory compound useful for treating diseases characterized by an immune disorder or inflammatory response. In another embodiment, CBP 505 (SEQ ID NO: 128) is an immune-modulating and/or anti-inflammatory compound useful for treating diseases characterized by an immune disorder or inflammatory response. In another embodiment, CBP 506 (SEQ ID NO: 129) is an immune-modulating and/or anti-inflammatory compound useful for treating diseases characterized by an immune disorder or inflammatory response. In another embodiment, CBP 510 (SEQ ID NO: 93) is an immune-modulating and/or anti-inflammatory compound useful for treating diseases characterized by an immune disorder or inflammatory response. In another embodiment, CBP 511 (SEQ ID NO: 94) is an immune-modulating and/or anti-inflammatory compound useful for treating diseases characterized by an immune disorder or inflammatory response. In another embodiment, CBP 512 (SEQ ID NO: 95) is an immune-modulating and/or anti-inflammatory compound useful for treating diseases characterized by an immune disorder or inflammatory response. In another embodiment, CBP 603 (SEQ ID NO: 89) is an immune-modulating and/or anti-inflammatory compound useful for treating diseases characterized by an immune disorder or inflammatory response.

Additional G2-checkpoint-abrogating compounds can be tested to determine their anti-inflammatory and/or immune-modulating activity as described herein, and compounds can be ranked by effectiveness with respect to each activity. In one embodiment, the anti-inflammatory activity and/or immune-modulating activity of exemplary peptides and peptidomimetics disclosed in Table 3 are evaluated, e.g., as described in Example 5, and structure-activity relationships can be developed for various uses including drug design.

Compound CBP501 Having Anti-viral Activity

In accordance with one aspect of the invention, compounds of the invention are CBP compounds with anti-viral activity as provided herein. As disclosed in U.S. application Ser. No. 10/347,145, CBP compounds can inhibit phosphorylation activities of variety of kinases involved in the cell cycle G2 checkpoint. CBP compounds bind 14-3-3 proteins, which are also involved in cell cycle G2 checkpoint signal transduction pathways. Human immunodeficiency virus type 1 (HIV-1), HIV-2, simian immunodeficiency virus and other lentiviruses have a viral protein vpr or related protein that may cause cell cycle G2 arrest (Jowett et al., *J. Virol.* 69:6304-13 (1995); Roshal et al., *J. Biol. Chem.* May 8, 2003; Stivahtis, et al., *J. Virol* 71:4331-8 (1997).). Vpr is required for replication of HIV-1 in lymphocytes and macrophages (Campbell and Hirsch, *J. Virol,* 71:5593-602 (1997); Subbramanian, et al., *J. Exp. Med.*, 187:1103-11 (1998)).

In accordance with a particular aspect of the invention, compound CBP501 (SEQ ID NO: 80) is an anti-viral compound as provided herein. As shown in Examples 3 and 4, CBP501 inhibited the replication of HIV-1 in vitro, demonstrating the anti-viral activity of G2 checkpoint abrogators such as CBP501.

In one embodiment, CBP501 inhibits HIV-1 replication. As shown in Example 3 and FIG. 1 infra, CBP501 showed antiviral activity in peripheral blood mononuclear cells (PBMC) by inhibiting replication of the clinical pediatric HIV strain WeJo; the $IC_{50}$ (concentration that inhibited virus replication by 50%) was determined to be =0.71 µg/ml CBP501, the $TC_{50}$ (concentration decreasing cell viability by 50%) was determined to be >80 µg/ml CBP501, and the TI (therapeutic index=$TC_{50}/IC_{50}$) was determined to be >113. It should be noted that CBP501 shows very low cell toxicity in vivo: at 80 µg/ml, the highest concentration tested in this emodiment, cell viability was hardly affected (see, FIG. 1). Given the low cell toxicity, that the calculation of $TC_{50}$=>80 µg/ml CBP501 is not a measurement of toxicity but rather, an estimate.

In another embodiment, CBP501 has antiviral activity against different HIV strains in different tissues. For example, CBP501 has inhibits replication of the WeJo strain of HIV-1 in PBMCs, and the Ba-L strain of HIV-1 in human monocyte/macrophage cells. As shown in Example 4 and FIG. 2, infra, CBP501 showed antiviral activity against HIV-1 by inhibiting replication of the Ba-L strain of HIV-1 in monocyte/macrophages, where the $IC_{50}$ was determined to be =6.5 µg/ml CBP501, the $TC_{50}$ was determined to be >80 µg/ml CBP501, and the TI (therapeutic index=$TC_{50}/IC_{50}$) was determined to be >12.3. It should be noted that CBP501 shows low cell toxicity in vivo: at 80 µg/ml, the highest concentration tested in this embodiment, cell viability was only decreased by about 25% (see, FIG. 2), such that the calculation of $TC_{50}$=>80 µg/ml CBP501 is not a measurement of toxicity but rather, an estimate.

CBP Compounds CBP500, CBP504, CBP505, CBP506, CBP510, CBP511, CBP512, and CBP603 Having Anti-viral Activity CBP compounds having G2 checkpoint abrogating activity similar to that of peptide CBP501 (SEQ ID NO: 80) include, but are not limited to, CBP500 (SEQ ID NO: 124), CBP 504 (SEQ ID NO: 127), CBP 505 (SEQ ID NO: 128), CBP 506 (SEQ ID NO: 129), CBP 510 (SEQ ID NO: 93), CBP 511 (SEQ ID NO: 94), CBP 512 (SEQ ID NO: 95), and CBP 603 (SEQ ID NO: 89). The sequences of all of the preceding CBP compounds are disclosed in Table 3. In one embodiment, CBP 500 (SEQ ID NO: 124) is an anti-viral compound useful for treating diseases characterized by viral infection. In another embodiment, CBP 504 (SEQ ID NO: 127) is an anti-viral compound useful for treating diseases characterized by viral infection. In another embodiment, CBP 505 (SEQ ID NO: 128) is an anti-viral compound useful for treating diseases characterized by viral infection. In another embodiment, CBP 506 (SEQ ID NO: 129) is an anti-viral compound useful for treating diseases characterized by viral infection. In another embodiment, CBP 510 (SEQ ID NO: 93) is an anti-viral compound useful for treating diseases characterized by viral infection. In another embodiment, CBP 511 (SEQ ID NO: 94) is an anti-viral compound useful for treating diseases characterized by viral infection. In another embodiment, CBP 512 (SEQ ID NO: 95) is an anti-viral compound useful for treating diseases characterized by viral infection. In another embodiment, CBP 603 (SEQ ID NO: 89) is an anti-viral compound useful for treating diseases characterized by viral infection.

Administration of Compounds and Pharmaceutical Compositions

The invention provides compounds that can be administered to achieve a desired effect. The invention further provides pharmaceutical compositions that can be administered to achieve a desired effect, wherein a pharmaceutical composition of the invention includes at least one compound of the invention and a pharmaceutically acceptable carrier or excipient, and may optionally include additional ingredients.

The invention provides combinations of at least one compound of the invention with a liposomal carrier. Such combinations are suitable for treating conditions such as HIV infection, where the virus is known to reside inside cells (e.g., monocyte/macrophage cells) and liposomes are also known to accumulate in those cells.

The invention provides combinations of at least one invention compound having a cell membrane permeant sequence to assist in traversing the cell membrane, as described above.

The compounds of the invention can be administered systemically, regionally (e.g., directed towards an organ or tissue), or locally (e.g., intracavity or topically onto the skin), in accordance with any protocol or route that achieves the desired effect. The compounds can be administered as a single or multiple dose each day (e.g., at a low dose), or intermittently (e.g., every other day, once a week, etc. at a higher dose). The compounds and pharmaceutical compositions can be administered via inhalation (e.g., intra-tracheal), oral, intravenous, intraarterial, intravascular, intrathecal, intraperitoneal, intramuscular, subcutaneous, intracavity, transdermal (e.g., topical), or transmucosal (e.g., buccal, vaginal, uterine, rectal, or nasal) delivery. The compounds and pharmaceutical compositions can be administered in multiple administrations, by sustained release (e.g., gradual perfusion over time) or in a single bolus.

The term "subject" refers to animals, typically mammalian animals, such as primates (humans, apes, gibbons, chimpanzees, orangutans, macaques), domestic animals (dogs, cats, birds), farm animals (horses, cattle, goats, sheep, pigs) and experimental animals (mouse, rat, rabbit, guinea pig). Subjects include animal disease models.

Amounts administered are typically in an "effective amount" or "sufficient amount" that is an amount sufficient to produce the desired affect. Effective amounts are therefore amounts that induce G2 checkpoint abrogation and one or more of: inhibiting or reducing susceptibility to inflammation, arthritis, auto-immune diseases, collagen diseases, allergy, asthma, pollinosis or atopy; decreasing one or more symptoms associated with inflammation, arthritis, auto-immune diseases, collagen diseases, allergy, asthma, pollinosis or atopy; inhibiting or reducing susceptibility to viral infection, especially HIV infection; decreasing one or more symptoms associated with viral infection, especially HIV infection.

Effective amounts can objectively or subjectively reduce or decrease the severity or frequency of symptoms associated with inflammation, arthritis, auto-immune diseases, collagen diseases, allergy, asthma, pollinosis or atopy, or an associated disorder or condition. For example, an amount of a compound of the invention that reduces itching, inflammation, pain, discharge or any other symptom or associated condition is an effective amount that produces a satisfactory clinical endpoint. Effective amounts also include a reduction of the amount (e.g., dosage) or frequency of treatment with another medicament to treat inflammation, arthritis, auto-immune diseases, collagen diseases, allergy, asthma, pollinosis or atopy, which is considered a satisfactory clinical endpoint.

Effective amounts can objectively or subjectively reduce or decrease the severity or frequency of symptoms associated with viral infection, especially HIV infection, or an associated disorder or condition. For example, an amount of a compound of the invention that reduces pain, fever, skin disorders, weight loss, nausea, diarrhea, or any other symptom or associated condition of viral infection is an effective amount that produces a satisfactory clinical endpoint. Effective amounts also include a reduction of the amount (e.g., dosage) or frequency of treatment with another anti-viral medicament, especially an anti-HIV medicament, which is considered a satisfactory clinical endpoint.

Methods of the invention that lead to an improvement in the subject's condition or a therapeutic benefit may be relatively short in duration, e.g., the improvement may last several hours, days or weeks, or extend over a longer period of time, e.g., months or years. An effective amount need not be a complete ablation of any or all symptoms of the condition or disorder. Thus, a satisfactory clinical endpoint for an effective amount is achieved when there is a subjective or objective improvement in the subjects' condition as determined using any of the foregoing criteria or other criteria known in the art appropriate for determining the status of the disorder or condition, over a short or long period of time. An amount effective to provide one or more beneficial effects, as described herein or known in the art, is referred to as an "improvement" of the subject's condition or "therapeutic benefit" to the subject.

An effective amount of an invention compound can be determined based upon animal studies or optionally in human clinical trials. The skilled artisan will appreciate the various factors that may influence the dosage or timing required to treat a particular subject including, for example, the general health, age, or gender of the subject, the severity or stage of the disorder or condition, previous treatments, susceptibility to undesirable side effects, clinical outcome desired or the presence of other disorders or conditions. Such factors may influence the dosage or timing required to provide an amount sufficient for therapeutic benefit.

Use of Compounds of the Invention for Screening

The present invention provides methods for using compounds of the invention to screen for compounds having anti-inflammatory and/or immune-modulating and/or anti-viral activity.

Test compounds can be screened using competitive assays including one or more peptide or peptidomimetic compounds of the invention, preferably using one or more compounds having a known therapeutic effect. In accordance with one aspect, the ability of a test compound to compete with a labelled compound of the invention for a binding site is determined by incubating tissue samples with a concentration series of test compound in the presence of a labelled compound of the invention, and measuring the amount of labelled compound bound to each tissue sample. It is understood that a decrease in the amount of labelled compound bound to the tissue sample in the presence of a known amount of test compound indicates the test compound competes for the same binding site as the labelled compound of the invention. For use in competitive screening assays, compounds of the invention can be labelled with any detectable label that does not interfere with the ability of the compound to bind to its site of action and elicit a therapeutic effect. Suitable labels include, but are not limited to, radioactive labels, fluorescent labels, chromogenic labels, biotin, streptavidin, and digoxin. One of skill in the art can use standard techniques to determine the binding affinity of the test compound for the binding site bound by the labelled compound of the invention.

In accordance with another aspect, the effectiveness of a test compound is determined by measuring the ability of a test compound to substitute for a therapeutic compound of the invention to elicit a known response in an assay system. It is understood that a therapeutic compound of the invention has immune-modulating and/or anti-inflammatory and/or anti-viral activity. It is further understood that the assay system for measuring the response elicited by a therapeutic compound of the invention may provide a direct measurement of immune-modulating and/or anti-inflammatory and/or anti-viral activity, e.g., in an animal model of a disease or a human subject suffering from the disease. Alternately, the assay system for measuring the response elicited by a therapeutic compound of the invention may provide an indirect measurement of immune-modulating and/or anti-inflammatory and/or anti-viral activity, by measuring e.g., gene expression, protein modification (e.g., kinase-mediated phosphorylation), release of mediators of immune or inflammatory responses, blocking of the effects of mediators of immune or inflammatory responses, cell differentiation, cell recruitment, cell proliferation, and so on. In one exemplary embodiment, test compounds are screened for the ability to inhibit histamine release, and the concentration of test compound required to cause a certain level of inhibition is compared with the concentration of a compound of the invention required to cause the same level of inhibition. In some embodiments, the therapeutic compound elicits a complex therapeutic response and the effectiveness of the therapeutic compound is determined by measuring, e.g., immune-modulating or anti-inflammatory effects in an animal model of human disease as described in Examples 1 and 2, or by anti-viral activity in a cell culture model of human disease as described in Examples 3 and 4. Test compounds can be screened for this ability to elicit the same therapeutic response in the assay system as that elicited by a therapeutic compound of the invention. In certain embodiments, test compounds and therapeutic compounds of the invention can be measured to the same assay system, providing a method whereby test compounds can be screened for their ability to potentiate (increase, enhance) the therapeutic response elicited by a compound of the invention.

In accordance with another aspect, compounds of the invention can be used to identify potentially effective compounds based on their structure, where structure-activity studies with compounds of the present invention, e.g., as described in Example 5, provide means for comparing the structure of an unknown test compound with the structure(s) of compounds of the invention having known anti-inflammatory and/or immune-modulating and/or anti-viral activity. Compounds of the invention can be used to generate a structure-activity database that can be used to evaluate and select test compounds to be screened. Such a structure-activity database can also be used to design new test compounds to screen, where the new test compounds are predicted to exhibit improved activity/properties and test the validity of the current structure-activity models. Predictions derived from the structure-activity database can be implemented by generating instructions for synthesis of new test compounds from selected combinations of the identified reagents.

A number of embodiments of the invention have been described. Nevertheless, it will be understood that various modifications may be made without departing from the spirit or scope of the invention. Accordingly, the following examples are intended to illustrate but not limit the scope of invention described in the claims.

EXAMPLES

Example 1

Activity of CBP501 Against Passive Cutaneous Anaphylaxis in Rats

CBP501 (SEQ ID NO: 80) was evaluated for anti-allergic activity in a model of passive cutaneous anaphylaxis (PCA) in Wistar rats. CBP501, at doses of 20, 10, and 5 mg/kg, was administered intraperitoneally (IP) 30 minutes before challenge with a mixture of ovalbumin and Evans Blue dye. CBP501 at 20, 10 and 5 mg/kg demonstrated highly significant anti-allergic effect, inhibiting by 93%, 93% and 87%, respectively, relative to vehicle control group. A trial using the antihistamine cyproheptadine-HCl was run concurrently as a control: cyproheptadine-HCl at 1 mg/kg, IP, exhibited a significant anti-allergic effect (87% inhibition).

Materials and Methods

CBP501 was dissolved in 0.9% NaCl. CBP501, at 20, 10 and 5 mg/kg, was administered intraperitoneally (IP) 30 min before challenge with a mixture of ovalbumin and Evans Blue dye.

Animals: Male or female Wistar rats were provided by the animal breeding center of MDS Pharma Services-Taiwan Ltd. Space allocation for 6 animals was 45×23×21 cm. All animals were maintained in a hygienic environment in a controlled temperature (21.5-22.5° C.) and humidity (50%-70%) environment, with 12 hour light-dark cycles for at least one week, housed in the MDS Pharma Services-Taiwan Laboratory, prior to being used. All aspects of this work including housing, experimentation and disposal of animals were performed in general accordance with the International Guiding Principles for Biomedical Research Involving Animals (CI-OMS Publication No. ISBN 92 90360194, 1985).

Chemicals: Cyproheptadine-HCl (RBI-USA), ethanol absolute (Merck, Germany), distilled water (in-house), Evans Blue (Fluka, Switzerland), and ovalbumin (Sigma-Aldrich, USA) were used.

Method of administration: Five groups of three (3) Wistar-derived male rats weighing 80+/−10 g were passively sensitized 16 hours earlier by intradermal injection of reaginic (IgE) antiovalbumin serum (0.05 ml) on two spots of the dorsal surface. CBP501 was administered at 5, 10 and 20 mg/kg IP. Within 30 minutes after administration of CBP501, the animals were challenged intravenously (IV) with a mixture of ovalbumin (1 mg) and Evans Blue dye (5 mg). Animals were sacrificed 30 minutes after challenge.

Results: Two measured weal diameters were averaged for each animal and scored 0 if <0.05 cm, 1 if 0.05-0.2 cm, 2 if 0.2-0.4 cm, 3 if 0.4-0.6 cm, 4 if 0.6-0.8 cm and 5 if >0.8 cm. Maximum possible score for each animal totals 2×5=10. Inhibition of the resulting PCA blue colored weal by 50 percent or more relative to the vehicle control group indicates possible antiallergic activity. Results are shown in Table 1, below, where significant changes are indicated by an asterisk(*).

TABLE 1

Effects of CBP501 on passive cutaneous anaphylaxis (PCA) in rats.

| Treatment | Route | Dose | N | PCA Response 1st Spot | PCA Response 2nd Spot | Total PCA Response | % Inhibition |
|---|---|---|---|---|---|---|---|
| Vehicle | IP | 5 ml/kg | 1 | 5 | 5 | 30 | 0 |
|  |  |  | 2 | 5 | 5 |  |  |
|  |  |  | 3 | 5 | 5 |  |  |
| CBP501 | IP | 20 mg/kg | 1 | 0 | 0 | 2 | 93* |
|  |  |  | 2 | 0 | 0 |  |  |
|  |  |  | 3 | 1 | 1 |  |  |
| CBP501 | IP | 10 mg/kg | 1 | 0 | 0 | 2 | 93* |
|  |  |  | 2 | 0 | 0 |  |  |
|  |  |  | 3 | 1 | 1 |  |  |
| CBP501 | IP | 5 mg/kg | 1 | 0 | 0 | 4 | 87* |
|  |  |  | 2 | 1 | 1 |  |  |
|  |  |  | 3 | 1 | 1 |  |  |
| Cyproheptadine | IP | 1 mg/kg | 1 | 0 | 0 | 4 | 87* |
|  |  |  | 2 | 1 | 1 |  |  |
|  |  |  | 3 | 1 | 1 |  |  |

Example 2

Activity of CBP501 Against Adjuvant-induced Arthritis

Test substance CBP501 (SEQ ID NO: 80) was evaluated for possible anti-inflammatory activity in Complete Freund's Adjuvant (CFA)-induced arthritis in rats. CFA is a water-in-oil emulsion containing mycobacterial cell wall components that, when used as an adjuvant, potentiate the humoral antibody response to injected antigens. Because CFA also stimulates a local immune response, injection of CFA alone provides a useful animal model for arthritis (adjuvant-induced arthritis). CBP501 was administered intraperitoneally (IP) at 10 mg/kg as a single dose, or at 2.5 and 5 mg/kg once daily for 5 consecutive days. The right hind paw volume was measured after CFA injection at 4 hours (denoted day 1) and on day 5, and the contralateral left hind paw volume was measured on days 14 and 18. In this model, CBP501 at 10 mg/kg (single dose) and 5 mg/kg (×5 doses) demonstrated significant anti-inflammatory activity in both acute and late phase. However, CBP501 at 2.5 mg/kg (×5 doses) exhibited only moderate but non-significant activity in acute phase, and no activity in late phase. A trial using hydrocortisone as a control was run concurrently: administration of hydrocortisone at 30 mg/kg daily for 5 days demonstrated significant activity in the acute phase and near-significant activity in the late phase. The results are shown in the table, where significant values are indicated by an asterisk (*). These results show that CBP501 at 10 mg/kg IP, or 5 mg/kg×5 IP, demonstrated significant anti-inflammatory activity in the CFA-induced arthritis in rats.

Materials and Methods

Test Substances and Dosing Pattern: CBP501 was dissolved in 0.9% NaCl and given in a volume of 5 ml/kg. CBP501 at 10 mg/kg was injected intraperitoneally (IP) once on day 1. CBP501 at 2.5 or 5 mg/kg, vehicle alone (vehicle control), or hydrocortisone (30 mg/kg) were each administered IP once daily for 5 consecutive days. The first dose was given 1 hour before challenge with CFA.

Animals: Male Lewis rats were obtained from Charles River Japan Inc. Space allocation for 6 animals was 45×23×21 cm. All animals were maintained in a controlled temperature (23-25° C.) and humidity (60-70%) environment, with 12-hour light-dark cycles for at least one week in MDS Pharma Services—Taiwan Laboratory prior to use. Free access to standard lab chow for rats (Lab Diet, Rodent Diet, PMI Nutrition International, USA) and tap water was granted. All aspects of this work including housing, experimentation and disposal of animals were performed in general accordance with the International Guiding Principles for Biomedical Research Involving Animals (CIOMS Publication No. ISBN 92 90360194, 1985).

Chemicals: Pyrogen free saline (Sintong, R.O.C.), hydrocortisone (Sigma-Aldrich, USA), mineral oil (Wako, Japan) and *Mycobacterium tuberculosis* (DIFCO, USA) were used.

Equipment: Animal cases (ShinTeh, R. O. C.), glass syringes (1 ml and 2 ml, Mitsuba, Japan), hypodermic needles (25 G×1", Top Corporation, Japan), plethysmometer (Cat. # 7150, UGO Basile, Italy), water cell (25 mm Diameter, Cat. # 7157, UGO Basile, Italy), rat scale (2.5 g ~500 g, Misaki, Japan) and rat oral needle (Natsume, Japan) were used for these trials.

Method: Five groups of 5 Lewis derived male rats weighing 160±10 g were used. Test substance CBP501 was administered intraperitoneally at 10 mg/kg (single dose) or at 2.5 and 5 mg/kg (once daily for 5 consecutive days). Complete Freund's Adjuvant (CFA) containing a suspension of killed *Mycobacterium tuberculosis* (0.3 mg in 0.1 ml of light mineral oil) was injected into the subplantar region of the right hind paw 1 hour after first dosing on first day (denoted day 1). Hind paw volume was measured by plethysmometer and water cell (25 mm diameter) on day 0 (before CFA challenge), day 1 and day 5 on the right paw (injected with CFA) and on days 0, 14, and 18 on the left paw (without CFA injection). Rats were weighed immediately before first dosing and 1 hour after final dosing. For CFA-injected vehicle control rats, the increase in paw volume on day 5 relative to day 1 (the acute phase of inflammation) is generally between 0.7 and 0.9 ml; that on day 18 relative to day 14 (the delayed phase of inflammation) is generally between 0.2 and 0.4 ml. Thus, anti-inflammatory activity in this model is determined by values calculated during the acute phase as well as the delayed phase. The animals were also weighed on Day 0 and Day 18; CFA-injected vehicle control animals generally gain between 20 to 50 g in body weight over this time period. A 30 percent or greater (>30%) reduction in paw volume relative to vehicle treated controls is considered significant. Results are shown in Table 2, below, where significant inhibition values (>30% compared with vehicle control) are indicated by an asterisk (*).

TABLE 2

Effect of CBP501 on development of adjuvant arthritis.

| Treatment | Route | Dose | % Inhibition relative to Days (1-5) | Vehicle treated control Days (14-18) |
|---|---|---|---|---|
| CBP501 | IP | 10 mg/kg | 61* | 31* |
| CBP501 | IP | 5 mg/kg per dose × 5 doses | 51* | 34* |
| CBP501 | IP | 2.5 mg/kg per dose × 5 doses | 27 | −11 |
| Hydrocortisone | PO | 30 mg/kg per dose × 5 doses | 42* | 29 |

Example 3

Inhibition of HIV-1 Replication in PBMC by CBP501

CBP501 was tested for antiviral activity against HIV-1 in peripheral blood mononuclear cells (PBMC) using the clinical pediatric HIV strain WeJo. PBMCs were derived from normal HIV-1-negative donors, and cultured under conditions which promote cell survival and HIV replication. Antiviral activity was measured by detecting the amount of extracellular HIV-1p24 protein in a sample, where a decrease in p24 levels indicated antiviral activity. Cytotoxicity was measured by a tetrazolium dye reduction method. Antiviral activity was analyzed for a series of dilutions of a stock solution of 100 μg/ml CBP501. The experiments were performed using serial dilutions of the compound, generating a series of concentrations from 0.3125 to 80 μg/ml CBP501. Results are shown in FIG. 1.

As shown in FIG. 1, the $IC_{50}$ (concentration that inhibited virus replication by 50%) was determined to be =0.71 μg/ml CBP501, the $TC_{50}$ (concentration decreasing cell viability by 50%) was determined to be >80 μg/ml CBP501 (it should be noted that at 80 μg/ml, the highest concentration tested, cell viability was hardly affected), and the TI (therapeutic index=$TC_{50}/IC_{50}$) was determined to be >113. Note that CBP501 was also called SF322 in FIG. 1.

Example 4

Inhibition of HIV-1 Replication in Human Macrophapes by CBP501

CBP501 was evaluated for antiviral activity in monocyte/macrophages using the HIV strain Ba-L. Monocyte/macrophages were derived from normal HIV-1-negative donors, and cultured under conditions which promote cell survival and HIV replication. Antiviral activity was measured by detecting the amount of extracellular HIV-1p24 protein in a sample, where a decrease in p24 levels indicated antiviral activity. Cytotoxity was measured by a tetrazolium dye reduction method. Antiviral activity was analyzed for a series of dilutions of a stock solution of 100 µg/ml CBP501. The experiments were performed using serial dilutions of the compound, generating a series of concentrations from 0.3125 to 80 µg/ml CBP501. Results are shown in FIG. 2.

Figure 2B:
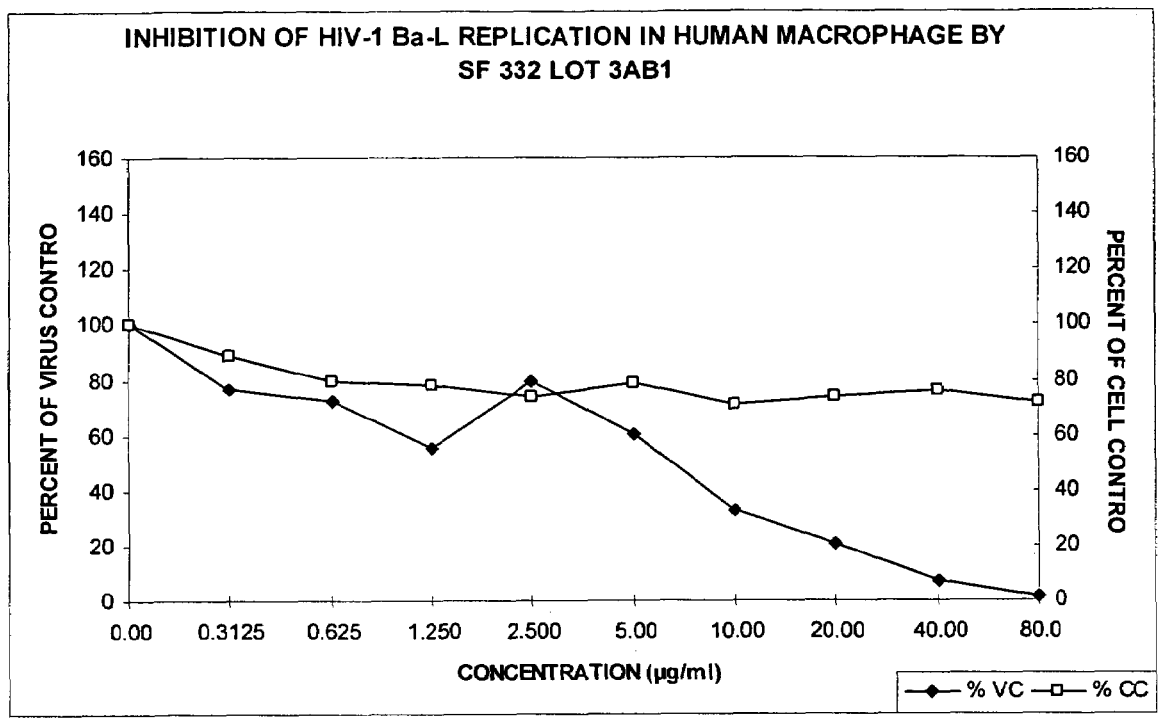

As shown in FIG. 2, the $IC_{50}$ (concentration that inhibited virus replication by 50%) was determined to be =6.5 µg/ml CBP501, the $TC_{50}$ (concentration decreasing cell viability by 50%) was determined to be >80 µg/ml CBP501 (it should be noted that at 80 µg/ml, the highest concentration tested, cell viability was only decreased by about 25%), and the TI (therapeutic index=$TC_{50}/IC_{50}$) was determined to be >12.3. Note that CBP501 was also called SF332 in FIG. 2.

Example 5

Structure-activity Relationships of Exemplary Peptides and Peptidomimetics of the Invention Exemplary peptides and peptidomimetics of the invention as shown in Table 3 are tested for anti-inflammatory, immune-modulating, and anti-viral activity as described in Examples 1-4, above. Structure-activity relationships can be determined by adapting methods disclosed in U.S. application Ser. No. 10/347,145. Briefly, structure-activity relationships of the exemplary compounds listed in Table 3 are determined by carrying out experiments to determine the effectiveness of each compound with respect to a class of activity, followed by ranking the compounds according to their effectiveness with respect to each class of activity, i.e., (a) anti-inflammatory activity; (b) immune-modulating activity; and/or (c) anti-viral activity. It is understood that one of skill in the art can select test systems to determine the effectiveness of each compound with respect to any class of activity for which a structure-activity determination is sought. It is further understood that one of skill in the art can select test systems that allow determination of more than one class of activity, e.g., a test system could include both an allergy model such as the PCA model described in Example 1 and an arthritic model described in Example 2, in order to measure both the immune-modulating activity and anti-inflammatory activity of compounds being tested.

To determine structure-activity relationships of the exemplary compounds listed in Table 3 with respect to anti-inflammatory activity, experiments are carried out to determine the effectiveness of each compound with respect its anti-inflammatory activity, e.g., using a test system as described in Example 2 above to quantitatively measure an inflammatory response, and the compounds are ranked according to their effectiveness as an anti-inflammatory agent in the test system. An arthritis model as described in Example 2 is also suitable to determine the effectiveness of compounds with respect to immune-modulating activity.

To determine structure-activity relationships of the exemplary compounds listed in Table 3 with respect to immune-modulating activity, experiments are carried out to determine the effectiveness of each compound with respect its immune-modulating activity, e.g., using a test system as described in Example 1 to quantitatively measure an immune response, and the compounds are ranked according to their effectiveness with respect to immune-modulating activity.

To determine structure-activity relationships of the exemplary compounds listed in Table 3 with respect to anti-viral activity, experiments are carried out to determine the effectiveness of each compound with respect its anti-viral activity, e.g., using a test system as described in Example 3 or 4 to quantitatively measure an indicator of viral infection (here, viral replication), and the compounds are ranked according to their effectiveness with respect to anti-viral activity.

For each class of activity, structure-activity relationships are determined by examining the structures of compounds having high levels of activity, moderate levels of activity, and low levels of activity, and identifying features common to compounds having desirable levels of activity.

TABLE 3

Sequences, SEQ ID NOs, and CBP code names of exemplary peptides and peptidomimetics

| Sequences of Peptides and Peptidomimetics | SEQ ID NO | CBP Code Name |
|---|---|---|
| (1-Tyr)(1-Gly)(1-Arg)(1-Lys)(1-Lys)(1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO:105 | CBP413 |
| (1-Tyr)(1-Gly)(1-Arg)(1-Lys)(1-Lys)(1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr) | SEQ ID NO:106 | CBP420 |
| (1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO:107 | CBP430 |
| (1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO:108 | CBP431 |
| (1-Arg)(1-Arg)(1-Gln)(1-Arg)(1-Arg)(1-Arg)(1-Cha)(1-Phe-2,3,4,5,6-F)(d-Ser)(d-Trp)(1-Pro)(1-Ser)(1-Tyr) | SEQ ID NO:109 | CBP432 |

TABLE 3-continued

Sequences, SEQ ID NOs, and CBP code names
of exemplary peptides and peptidomimetics

| Sequences of Peptides and Peptidomimetics | SEQ ID NO | CBP Code Name |
|---|---|---|
| (l-Tyr)(l-Gly)(l-Arg)(l-Lys)(l-Lys)(l-Arg)(l-Arg)(l-Gln)(l-Arg)(l-Arg)(l-Arg)(l-Cha)(l-Phe-2,3,4,5,6-F)(l-aminoundecanoic acid)(l-Tyr)(l-Tyr) | SEQ ID NO:110 | CBP440 |
| (d-Tyr)(d-Tyr)(d-Ser)(l-Gly)(d-Ser)(d-Arg)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | SEQ ID NO:111 | CBP450 |
| (d-Tyr)(d-Ser)(d-Pro)(l-Trp)(l-Ser)(d-Phe-2,3,4,5,6-F)(d-Cha)(d-Arg)(d-Arg)(d-Arg)(d-Gln)(d-Arg)(d-Arg) | SEQ ID NO:87 | CBP451 |
| (d-Tyr)(d-Ser)(l-Pro)(l-Trp)(l-Ser)(d-Phe-2,3,4,5,6-F)(d-Cha)(d-Arg)(d-Arg)(d-Arg)(d-Gln)(d-Arg)(d-Arg) | SEQ ID NO:88 | CBP452 |
| (d-Tyr)(d-Ser)(d-Pro)(l-Trp)(l-Ser)(d-Phe-2,3,4,5,6-F)(d-Pro)(d-Arg)(d-Arg)(d-Arg)(d-Gln)(d-Arg)(d-Arg) | SEQ ID NO:112 | CBP454 |
| (d-Tyr)(d-Ser)(l-Pro)(l-Trp)(l-Ser)(d-Phe-2,3,4,5,6-F)(l-Pro)(d-Arg)(d-Arg)(d-Arg)(d-Gln)(d-Arg)(d-Arg) | SEQ ID NO:113 | CBP455 |
| (l-Tyr)(l-Tyr)(l-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | SEQ ID NO:114 | CBP460 |
| (l-Tyr)(l-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | SEQ ID NO:115 | CBP461 |
| (l-Tyr)(l-aminoundecanoic acid)(d-Phe-2,3,4,5,6-F)(d-Cha) | SEQ ID NO:116 | CBP462 |
| (l-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | SEQ ID NO:117 | CBP463 |
| (l-aminoundecanoic acid)(d-Phe-2,3,4,5,6-F)(d-Cha) | SEQ ID NO:118 | CBP464 |
| (l-aminoundecanoic acid)(d-Phe-2,3,4,5,6-F)(d-Cha)(d-Arg)(d-Arg)(d-Arg)(d-Gln)(d-Arg)(d-Arg) | SEQ ID NO:119 | CBP465 |
| (l-8-aminocaprylic acid)(d-Cha)(d-Phe-2,3,4,5,6-F)(d-Arg)(d-Arg)(d-Arg)(d-Gln)(d-Arg)(d-Arg) | SEQ ID NO:120 | CBP466 |
| (d-Phe-2,3,4,5,6-F)(d-Cha) | SEQ ID NO:121 | CBP470 |
| (d-Cha)(d-Phe-2,3,4,5,6-F)(d-Arg)(d-Arg)(d-Arg)(d-Gln)(d-Arg)(d-Arg) | SEQ ID NO:122 | CBP471 |
| (d-Tyr)(d-Ser)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO:123 | CBP481 |
| (d-Tyr)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO:124 | CBP500 |
| (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO:80 | CBP501 |
| (d-Bpa)(l-8-aminocaprylic acid)(d-Cha)(d-Phe-2,3,4,5,6-F)(d-Arg)(d-Arg)(d-Arg)(d-Gln)(d-Arg)(d-Arg) | SEQ ID NO:125 | CBP502 |
| (d-Bpa)(l-8-aminocaprylic acid)(d-Phe-2,3,4,5,6-F)(d-Cha)(d-Arg)(d-Arg)(d-Arg)(d-Gln)(d-Arg)(d-Arg) | SEQ ID NO:126 | CBP503 |
| (d-Asp)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO:127 | CBP504 |
| (d-Bpa)(d-Asp)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO:128 | CBP505 |
| (d-Bpa)(d-Ser)(d-Trp)(d-Ser)(d-Asp)(d-Phe-2,3,4,5,6-F)(d-Cha)(d-Arg)(d-Arg)(d-Arg)(d-Gln)(d-Arg)(d-Arg) | SEQ ID NO:129 | CBP506 |
| (d-Arg)(d-Arg)(d-Arg)(d-Gln)(d-Arg)(d-Arg)(d-Cha)(d-Phe-2,3,4,5,6-F)(d-Ser)(d-Trp)(d-Ser)(d-Bpa) | SEQ ID NO:93 | CBP510 |
| (d-Arg)(d-Arg)(d-Arg)(d-Gln)(d-Arg)(d-Arg)(d-Bpa)(d-Ser)(d-Trp) | SEQ ID NO:94 | CBP511 |

TABLE 3-continued

Sequences, SEQ ID NOs, and CBP code names of exemplary peptides and peptidomimetics

| Sequences of Peptides and Peptidomimetics | SEQ ID NO | CBP Code Name |
|---|---|---|
| (d-Ser)(d-Phe-2,3,4,5,6-F)(d-Cha) | | |
| (d-Arg)(d-Arg)(d-Arg)(d-Arg)(d-Arg)(d-Arg)(d-Cha)(d-Phe-2,3,4,5,6-F)(d-Ser)(d-Trp)(d-Ser)(d-Bpa) | SEQ ID NO:95 | CBP512 |
| (d-Bpa)(d-Ser)(d-Trp)(d-Ser)(d-Bpa)(d-Cha)(d-Arg)(d-Arg)(d-Arg)(d-Gln)(d-Arg)(d-Arg) | SEQ ID NO:130 | CBP601 |
| (d-Bpa)(1-8-aminocaprylic acid)(d-Bpa)(d-Cha)(d-Arg)(d-Arg)(d-Arg)(d-Gln)(d-Arg)(d-Arg) | SEQ ID NO:131 | CBP602 |
| (d-Bpa)(d-Ser)(d-Trp)(d-Ser)(d-Phe4No2)(d-Cha)(d-Arg)(d-Arg)(d-Arg)(d-Gln)(d-Arg)(d-Arg) | SEQ ID NO:89 | CBP603 |
| (d-Bpa)(d-Pro)(d-Trp)(d-Pro)(d-Phe4No2)(d-Cha)(d-Arg)(d-Arg)(d-Arg)(d-Gln)(d-Arg)(d-Arg) | SEQ ID NO:132 | CBP604 |
| (d-Bpa)(d-Pro)(d-Trp)(d-Pro)(d-Phe4No2)(d-Nal2)(d-Arg)(d-Arg)(d-Arg)(d-Gln)(d-Arg)(d-Arg) | SEQ ID NO:133 | CBP605 |
| (d-Phe4NO2)(d-Pro)(d-Trp)(d-Pro)(d-Phe4NO2)(d-Cha)(d-Arg)(d-Arg)(d-Arg)(d-Gln)(d-Arg)(d-Arg) | SEQ ID NO:134 | CBP606 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg) | SEQ ID NO:90 | CBP607 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg)(d-Arg) | SEQ ID NO:91 | CBP608 |
| (d-Bpa)(d-Ser)(d-Trp)(d-Ser)(d-Phe-2,3,4,5,6-F)(d-Cha)(d-Lys)(d-Lys)(d-Lys)(d-Lys)(d-Lys) | SEQ ID NO:92 | CBP609 |
| (d-Arg)(d-Arg)(d-Bpa)(d-Arg)(d-Arg)(d-Arg)(d-Phe-2,3,4,5,6-F)(d-Cha) | SEQ ID NO:96 | CBP700 |
| (d-Arg)(d-Arg)(d-Arg)(d-Bpa)(d-Arg)(d-Trp)(d-Arg)(d-Phe-2,3,4,5,6-F)(d-Cha) | SEQ ID NO:97 | CBP701 |
| (d-Arg)(d-Arg)(d-Arg)(d-Arg)(d-Bpa)(d-Arg)(d-Trp)(d-Arg)(d-Phe-2,3,4,5,6-F)(d-Cha) | SEQ ID NO:98 | CBP702 |
| (d-Arg)(d-Arg)(d-Arg)(d-Bpa)(d-Arg)(d-Arg)(d-Arg)(d-Phe-2,3,4,5,6-F)(d-Cha) | SEQ ID NO:99 | CBP703 |
| (d-Bpa)(d-Cys)(d-Trp)(d-Arg)(d-Phe-2,3,4,5,6F)(d-Cha)(d-Cys) | SEQ ID NO:135 | CBP524 |
| (d-Tyr)(d-Cys)(d-Pro)(d-Trp)(d-Arg)(d-Phe-2,3,4,5,6F)(d-Cha)(d-Cys) | SEQ ID NO:136 | CBP721 |

What is claimed is:

1. A method of treating a disease selected from the group consisting of inflammation and arthritis by administering to a subject in need thereof an effective amount of a G2-checkpoint-abrogating peptide or peptidomimetic comprising the structure selected from the group consisting of CBP500 (SEQ ID NO: 124), CBP501 (SEQ ID NO:80), CBP504 (SEQ ID NO: 127), CBP505 (SEQ ID NO: 128), CBP506 (SEQ ID NO: 129), CBP510 (SEQ ID NO:93), CBP511 (SEQ ID NO:94), CBP512 (SEQ ID NO:95), and CBP603 (SEQ ID NO:89).

2. The method of claim 1, comprising administering CBP500 (SEQ ID NO: 124).

3. The method of claim 1, comprising administering CBP501 (SEQ ID NO: 80).

4. The method of claim 1, comprising administering CBP504 (SEQ ID NO: 127).

5. The method of claim 1, comprising administering CBP505 (SEQ ID NO: 128).

6. The method of claim 1, comprising administering CBP506 (SEQ ID NO: 129).

7. The method of claim 1, comprising administering CBP510 (SEQ ID NO: 93).

8. The method of claim 1, comprising administering CBP511 (SEQ ID NO: 94).

9. The method of claim 1, comprising administering CBP512 (SEQ ID NO: 95).

10. The method of claim 1, comprising administering CBP603 (SEQ ID NO: 89).

* * * * *

SEQUENCE LISTING

<160> NUMBER OF SEQ ID NOS: 255

<210> SEQ ID NO 1

<400> SEQUENCE: 1

000

<210> SEQ ID NO 2

<400> SEQUENCE: 2

000

```
<210> SEQ ID NO 3
<400> SEQUENCE: 3
000

<210> SEQ ID NO 4
<400> SEQUENCE: 4
000

<210> SEQ ID NO 5
<400> SEQUENCE: 5
000

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
```

-continued

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

```
<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
```

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59
<211> LENGTH: 12
<212> TYPE: PRT

```
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Cyclohexyl-alanine

<400> SEQUENCE: 59

Xaa Ser Trp Ser Phe Xaa Arg Arg Gln Arg Arg Arg
1               5                   10

<210> SEQ ID NO 60
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Benzoyl-phenylalanine
<220> FEATURE:
<221> NAME/KEY: SITE
<222> LOCATION: (11)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Cyclohexyl-alanine

<400> SEQUENCE: 60

Arg Arg Gln Arg Arg Arg Xaa Ser Trp Ser Xaa Xaa
1               5                   10

<210> SEQ ID NO 61
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 61
```

```
Xaa Xaa Ser Trp Ser Xaa Arg Arg Arg Gln Arg Arg
1               5                   10

<210> SEQ ID NO 62
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Cyclohexyl-alanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Benzoyl-phenylalanine

<400> SEQUENCE: 62

Arg Arg Arg Gln Arg Arg Xaa Xaa Ser Trp Ser Xaa
1               5                   10

<210> SEQ ID NO 63
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 63

Xaa Xaa Ser Trp Ser Xaa Arg Arg Gln Arg Arg Arg
1               5                   10

<210> SEQ ID NO 64
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Cyclohexyl-alanine
```

```
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Benzoyl-phenylalanine

<400> SEQUENCE: 64

Arg Arg Gln Arg Arg Arg Xaa Xaa Ser Trp Ser Xaa
1               5                   10

<210> SEQ ID NO 65
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Cyclohexyl-alanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Benzoyl-phenylalanine

<400> SEQUENCE: 65

Arg Arg Arg Arg Arg Arg Xaa Xaa Ser Trp Ser Xaa
1               5                   10

<210> SEQ ID NO 66
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 66

Xaa Xaa Ser Trp Ser Xaa Arg Arg Arg Arg Arg Arg
1               5                   10

<210> SEQ ID NO 67
<211> LENGTH: 12
<212> TYPE: PRT
<213> ORGANISM: Artificial sequence
```

```
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Benzoyl-phenylalanine
<220> FEATURE:
<221> NAME/KEY: SITE
<222> LOCATION: (11)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Cyclohexyl-alanine

<400> SEQUENCE: 67

Arg Arg Arg Arg Arg Arg Xaa Ser Trp Ser Xaa Xaa
1               5                   10

<210> SEQ ID NO 68
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 68

Xaa Ser Trp Ser Xaa Xaa Arg Arg Arg Arg Arg Arg
1               5                   10

<210> SEQ ID NO 69
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (3)
<223> OTHER INFORMATION: Xaa is D-Benzoyl-phenylalanine
<220> FEATURE:
<221> NAME/KEY: SITE
<222> LOCATION: (7)
<223> OTHER INFORMATION: Xaa is D-Phenylalanine-2,3,4,5,6-F
<220> FEATURE:
<221> NAME/KEY: SITE
<222> LOCATION: (8)
<223> OTHER INFORMATION: Xaa is D-Cyclohexyl-alanine
```

```
<400> SEQUENCE: 69

Arg Arg Xaa Arg Arg Arg Xaa Xaa
1               5

<210> SEQ ID NO 70
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 70

Xaa Xaa Arg Arg Arg Xaa Arg Arg
1               5

<210> SEQ ID NO 71
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (4)
<223> OTHER INFORMATION: Xaa is D-Benzoyl-phenylalanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (9)
<223> OTHER INFORMATION: Xaa is D-Cyclohexyl-alanine

<400> SEQUENCE: 71

Arg Arg Arg Xaa Arg Trp Arg Xaa Xaa
1               5

<210> SEQ ID NO 72
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
```

```
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 72

Xaa Xaa Arg Trp Arg Xaa Arg Arg Arg
1               5

<210> SEQ ID NO 73
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(10)
<223> OTHER INFORMATION: Positions 1 to 10 are D-amino acids
<220> FEATURE:
<221> NAME/KEY: SITE
<222> LOCATION: (5)
<223> OTHER INFORMATION: Xaa is D-Benzoyl-phenylalanine
<220> FEATURE:
<221> NAME/KEY: SITE
<222> LOCATION: (9)
<223> OTHER INFORMATION: Xaa is D-Phenylalanine-2,3,4,5,6-F
<220> FEATURE:
<221> NAME/KEY: SITE
<222> LOCATION: (10)
<223> OTHER INFORMATION: Xaa is D-Cyclohexyl-alanine

<400> SEQUENCE: 73

Arg Arg Arg Arg Xaa Arg Trp Arg Xaa Xaa
1               5                   10

<210> SEQ ID NO 74
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(10)
<223> OTHER INFORMATION: Positions 1 to 10 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 74

Xaa Xaa Arg Trp Arg Xaa Arg Arg Arg Arg
1               5                   10

<210> SEQ ID NO 75
```

```
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (4)
<223> OTHER INFORMATION: Xaa is D-Benzoyl-phenylalanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (9)
<223> OTHER INFORMATION: Xaa is D-Cyclohexyl-alanine

<400> SEQUENCE: 75

Arg Arg Arg Xaa Arg Arg Arg Xaa Xaa
1               5

<210> SEQ ID NO 76
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Benzoyl-phenylalanine

<400> SEQUENCE: 76

Xaa Xaa Arg Arg Arg Xaa Arg Arg Arg
1               5

<210> SEQ ID NO 77
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
```

```
<221> NAME/KEY: SITE
<222> LOCATION: (6)
<223> OTHER INFORMATION: Xaa is D-Cyclohexyl-alanine

<400> SEQUENCE: 77

Xaa Ser Trp Ser Xaa Xaa Arg Arg Arg Gln Arg Arg
1               5                   10

<210> SEQ ID NO 78

<400> SEQUENCE: 78

000

<210> SEQ ID NO 79

<400> SEQUENCE: 79

000

<210> SEQ ID NO 80
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 80

Xaa Ser Trp Ser Xaa Xaa Arg Arg Arg Gln Arg Arg
1               5                   10

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84
```

000

<210> SEQ ID NO 85

<400> SEQUENCE: 85

000

<210> SEQ ID NO 86

<400> SEQUENCE: 86

000

<210> SEQ ID NO 87
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(3)
<223> OTHER INFORMATION: Positions 1 to 3 are D-amino acids
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 87

Tyr Ser Pro Trp Ser Xaa Xaa Arg Arg Arg Gln Arg Arg
1               5                   10

<210> SEQ ID NO 88
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 88

Tyr Ser Pro Trp Ser Xaa Xaa Arg Arg Arg Gln Arg Arg
1               5                   10

<210> SEQ ID NO 89
<211> LENGTH: 12

```
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-4NO2
<220> FEATURE:
<221> NAME/KEY: SITE
<222> LOCATION: (6)
<223> OTHER INFORMATION: Xaa is D-Cyclohexyl-alanine

<400> SEQUENCE: 89

Xaa Ser Trp Ser Xaa Xaa Arg Arg Arg Gln Arg Arg
1               5                   10

<210> SEQ ID NO 90
<211> LENGTH: 11
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(11)
<223> OTHER INFORMATION: Positions 1 to 11 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 90

Xaa Ser Trp Ser Xaa Xaa Arg Arg Arg Arg Arg
1               5                   10

<210> SEQ ID NO 91
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
```

```
<222> LOCATION: (6)
<223> OTHER INFORMATION: Xaa is D-Cyclohexyl-alanine

<400> SEQUENCE: 91

Xaa Ser Trp Ser Xaa Xaa Arg Arg Arg Arg Arg Arg
1               5                   10

<210> SEQ ID NO 92
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 92

Xaa Ser Trp Ser Xaa Xaa Lys Lys Lys Lys Lys Lys
1               5                   10

<210> SEQ ID NO 93
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Cyclohexyl-alanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Benzoyl-phenylalanine

<400> SEQUENCE: 93

Arg Arg Arg Gln Arg Arg Xaa Xaa Ser Trp Ser Xaa
1               5                   10

<210> SEQ ID NO 94
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
```

```
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Benzoyl-phenylalanine
<220> FEATURE:
<221> NAME/KEY: SITE
<222> LOCATION: (11)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Cyclohexyl-alanine

<400> SEQUENCE: 94

Arg Arg Arg Gln Arg Arg Xaa Ser Trp Ser Xaa Xaa
1               5                   10

<210> SEQ ID NO 95
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)
<223> OTHER INFORMATION: Xaa is D-Cyclohexyl-alanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Benzoyl-phenylalanine

<400> SEQUENCE: 95

Arg Arg Arg Arg Arg Arg Xaa Xaa Ser Trp Ser Xaa
1               5                   10

<210> SEQ ID NO 96
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (3)
<223> OTHER INFORMATION: Xaa is D-Benzoyl-phenylalanine
<220> FEATURE:
<221> NAME/KEY: SITE
<222> LOCATION: (7)
<223> OTHER INFORMATION: Xaa is D-Phenylalanine-2,3,4,5,6-F
<220> FEATURE:
<221> NAME/KEY: SITE
<222> LOCATION: (8)
<223> OTHER INFORMATION: Xaa is D-Cyclohexyl-alanine

<400> SEQUENCE: 96

Arg Arg Xaa Arg Arg Arg Xaa Xaa
1               5
```

```
<210> SEQ ID NO 97
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (4)
<223> OTHER INFORMATION: Xaa is D-Benzoyl-phenylalanine
<220> FEATURE:
<221> NAME/KEY: SITE
<222> LOCATION: (8)
<223> OTHER INFORMATION: Xaa is D-Phenylalanine-2,3,4,5,6-F
<220> FEATURE:
<221> NAME/KEY: SITE
<222> LOCATION: (9)
<223> OTHER INFORMATION: Xaa is D-Cyclohexyl-alanine

<400> SEQUENCE: 97

Arg Arg Arg Xaa Arg Trp Arg Xaa Xaa
1               5

<210> SEQ ID NO 98
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(10)
<223> OTHER INFORMATION: Positions 1 to 10 are D-amino acids
<220> FEATURE:
<221> NAME/KEY: SITE
<222> LOCATION: (5)
<223> OTHER INFORMATION: Xaa is D-Benzoyl-phenylalanine
<220> FEATURE:
<221> NAME/KEY: SITE
<222> LOCATION: (9)
<223> OTHER INFORMATION: Xaa is D-Phenylalanine-2,3,4,5,6-F
<220> FEATURE:
<221> NAME/KEY: SITE
<222> LOCATION: (10)
<223> OTHER INFORMATION: Xaa is D-Cyclohexyl-alanine

<400> SEQUENCE: 98

Arg Arg Arg Arg Xaa Arg Trp Arg Xaa Xaa
1               5                   10

<210> SEQ ID NO 99
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (4)
<223> OTHER INFORMATION: Xaa is D-Benzoyl-phenylalanine
<220> FEATURE:
<221> NAME/KEY: SITE
<222> LOCATION: (8)
```

<223> OTHER INFORMATION: Xaa is D-Phenylalanine-2,3,4,5,6-F
<220> FEATURE:
<221> NAME/KEY: SITE
<222> LOCATION: (9)
<223> OTHER INFORMATION: Xaa is D-Cyclohexyl-alanine

<400> SEQUENCE: 99

Arg Arg Arg Xaa Arg Arg Arg Xaa Xaa
1               5

<210> SEQ ID NO 100
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 11 are D-amino acids
<220> FEATURE:
<221> NAME/KEY: SITE
<222> LOCATION: (7)
<223> OTHER INFORMATION: Xaa is D-Benzoyl-phenylalanine
<220> FEATURE:
<221> NAME/KEY: SITE
<222> LOCATION: (11)
<223> OTHER INFORMATION: Xaa is D-Phenylalanine-2,3,4,5,6-F
<220> FEATURE:
<221> NAME/KEY: SITE
<222> LOCATION: (12)
<223> OTHER INFORMATION: Xaa is D-Cyclohexyl-alanine

<400> SEQUENCE: 100

Arg Arg Arg Gln Arg Arg Xaa Ser Trp Ser Xaa Xaa
1               5                   10

<210> SEQ ID NO 101
<211> LENGTH: 6
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(6)
<223> OTHER INFORMATION: Positions 1 to 6 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 101

Xaa Ser Trp Ser Xaa Xaa
1               5

<210> SEQ ID NO 102
<211> LENGTH: 7
<212> TYPE: PRT
<213> ORGANISM: Artificial sequence
<220> FEATURE:
<223> OTHER INFORMATION: Description of artificial sequence: Synthetic
      peptide

```
<220> FEATURE:
<221> NAME/KEY: SITE
<222> LOCATION: (1)..(7)
<223> OTHER INFORMATION: Positions 1 to 7 are D-amino acids
<220> FEATURE:
<221> NAME/KEY: SITE
<222> LOCATION: (6))
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 102

Tyr Ser Pro Trp Ser Xaa Xaa
1               5

SEQ ID NO 103
LENGTH: 7
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(7)
<223> OTHER INFORMATION: Positions 1 to 7 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 103

Xaa Cys Trp Ser Xaa Xaa Cys
1               5

<210> SEQ ID NO 104
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (6)
<223> OTHER INFORMATION: Xaa is D-Phenylalanine-2,3,4,5,6-FPositions 1
      to 11 are D-amino acids
<220> FEATURE:
<221> NAME/KEY: SITE
<222> LOCATION: (7)
<223> OTHER INFORMATION: Xaa is D-Cyclohexyl-alanine

<400> SEQUENCE: 104

Tyr Cys Pro Trp Ser Phe Xaa Cys
1               5

SEQ ID NO 105
LENGTH: 19
<212> TYPE: PRT
```

```
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (12)
<223> OTHER INFORMATION: Xaa is Cyclohexyl-alanine
<220> FEATURE:
<221> NAME/KEY: SITE
<222> LOCATION: (13)
<223> OTHER INFORMATION: Xaa is D-Phenylalanine-2,3,4,5,6-F

<400> SEQUENCE: 105

Tyr Gly Arg Lys Lys Arg Arg Gln Arg Arg Xaa Xaa Arg Ser Pro
1               5                   10                  15

Ser Tyr Tyr

<210> SEQ ID NO 106
<211> LENGTH: 18
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (12)
<223> OTHER INFORMATION: Xaa is Cyclohexyl-alanine
<220> FEATURE:
<221> NAME/KEY: SITE
<222> LOCATION: (13)
<223> OTHER INFORMATION: Xaa is Phenylalanine-2,3,4,5,6-F

<400> SEQUENCE: 106

Tyr Gly Arg Lys Lys Arg Arg Gln Arg Arg Xaa Xaa Arg Ser Pro
1               5                   10                  15

Ser Tyr

<210> SEQ ID NO 107
<211> LENGTH: 11
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (4)
<223> OTHER INFORMATION: Xaa is Cyclohexyl-alanine
<220> FEATURE:
<221> NAME/KEY: SITE
<222> LOCATION: (5)
<223> OTHER INFORMATION: Xaa is Phenylalanine-2,3,4,5,6-F

<400> SEQUENCE: 107

Arg Arg Arg Xaa Xaa Arg Ser Pro Ser Tyr Tyr
1               5                   10

<210> SEQ ID NO 108
<211> LENGTH: 14
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (7)
<223> OTHER INFORMATION: Xaa is Cyclohexyl-alanine
<220> FEATURE:
```

```
<221> NAME/KEY: SITE
<222> LOCATION: (8)
<223> OTHER INFORMATION: Xaa is Phenylalanine-2,3,4,5,6-F

<400> SEQUENCE: 108

Arg Arg Gln Arg Arg Xaa Xaa Arg Ser Pro Ser Tyr Tyr
1               5                   10

<210> SEQ ID NO 109
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (9)..(10)
<223> OTHER INFORMATION: Positions 9 and 10 are D-amino acids
<220> FEATURE:
<221> NAME/KEY: SITE
<222> LOCATION: (7)
<223> OTHER INFORMATION: Xaa is Cyclohexyl-alanine
<220> FEATURE:
<221> NAME/KEY: SITE
<222> LOCATION: (8)
<223> OTHER INFORMATION: Xaa is Phenylalanine-2,3,4,5,6-F

<400> SEQUENCE: 109

Arg Arg Gln Arg Arg Arg Xaa Xaa Ser Trp Pro Ser Tyr
1               5                   10

<210> SEQ ID NO 110
<211> LENGTH: 16
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (12)
<223> OTHER INFORMATION: Xaa is Cyclohexyl-alanine
<220> FEATURE:
<221> NAME/KEY: SITE
<222> LOCATION: (13)
<223> OTHER INFORMATION: Xaa is Phenylalanine-2,3,4,5,6-F
<220> FEATURE:
<221> NAME/KEY: SITE
<222> LOCATION: (14)
<223> OTHER INFORMATION: Xaa is aminoundecanoic acid

<400> SEQUENCE: 110

Tyr Gly Arg Lys Lys Arg Arg Gln Arg Arg Xaa Xaa Xaa Tyr Tyr
1               5                   10                  15

<210> SEQ ID NO 111
<211> LENGTH: 19
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(3)
<223> OTHER INFORMATION: Positions 1 to 3 are D-amino acids
<220> FEATURE:
<221> NAME/KEY: SITE
<222> LOCATION: (5)..(17)
<223> OTHER INFORMATION: Positions 5 to 17 are D-amino acids
<220> FEATURE:
<221> NAME/KEY: SITE
```

```
<222> LOCATION: (7)
<223> OTHER INFORMATION: Xaa is D-Phenylalanine-2,3,4,5,6-F
<220> FEATURE:
<221> NAME/KEY: SITE
<222> LOCATION: (8)
<223> OTHER INFORMATION: Xaa is D-Cyclohexyl-alanine
<220> FEATURE:
<221> NAME/KEY: SITE
<222> LOCATION: (19)
<223> OTHER INFORMATION: Tyr is D-Tyr

<400> SEQUENCE: 111

Tyr Tyr Ser Gly Ser Arg Phe Xaa Arg Arg Arg Gln Arg Arg Lys Lys
1               5                   10                  15

Arg Gly Tyr

<210> SEQ ID NO 112
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(3)
<223> OTHER INFORMATION: Positions 1 to 3 are D-amino acids
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)
<223> OTHER INFORMATION: Xaa is D-Phenylalanine-2,3,4,5,6-F

<400> SEQUENCE: 112

Tyr Ser Pro Trp Ser Xaa Pro Arg Arg Arg Gln Arg Arg
1               5                   10

<210> SEQ ID NO 113
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (8)..(13)
<223> OTHER INFORMATION: Positions 8 to 13 are D-amino acids
<220> FEATURE:
<221> NAME/KEY: SITE
<222> LOCATION: (6)
<223> OTHER INFORMATION: Phe is D-Phenylalanine-2,3,4,5,6-F

<400> SEQUENCE: 113

Tyr Ser Pro Trp Ser Xaa Pro Arg Arg Arg Gln Arg Arg
1               5                   10

<210> SEQ ID NO 114
<211> LENGTH: 16
<212> TYPE: PRT
<213> ORGANISM: Artificial sequence
<220> FEATURE:
<223> OTHER INFORMATION: Description of artificial sequence: Synthetic
      peptide
<220> FEATURE:
```

```
<221> NAME/KEY: SITE
<222> LOCATION: (4)..(14)
<223> OTHER INFORMATION: Positions 4 to 14 are D-amino acids
<220> FEATURE:
<221> NAME/KEY: SITE
<222> LOCATION: (3)
<223> OTHER INFORMATION: Xaa is aminoundecanoic acid
<220> FEATURE:
<221> NAME/KEY: SITE
<222> LOCATION: (4)
<223> OTHER INFORMATION: Xaa is D-Phenylalanine-2,3,4,5,6-F
<220> FEATURE:
<221> NAME/KEY: SITE
<222> LOCATION: (5)
<223> OTHER INFORMATION: Xaa is D-Cyclohexyl-alanine
<220> FEATURE:
<221> NAME/KEY: SITE
<222> LOCATION: (16)
<223> OTHER INFORMATION: Tyr is D-Tyr

<400> SEQUENCE: 114

Tyr Tyr Xaa Xaa Xaa Arg Arg Arg Gln Arg Arg Lys Lys Arg Gly Tyr
1               5                   10                  15

<210> SEQ ID NO 115
<211> LENGTH: 15
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (3)..(13)
<223> OTHER INFORMATION: Positions 3 to 13 are D-amino acids
<220> FEATURE:
<221> NAME/KEY: SITE
<222> LOCATION: (2)
<223> OTHER INFORMATION: Xaa is aminoundecanoic acid
<220> FEATURE:
<221> NAME/KEY: SITE
<222> LOCATION: (3)
<223> OTHER INFORMATION: Xaa is D-Phenylalanine-2,3,4,5,6-F
<220> FEATURE:
<221> NAME/KEY: SITE
<222> LOCATION: (4)
<223> OTHER INFORMATION: Xaa is D-Cyclohexyl-alanine
<220> FEATURE:
<221> NAME/KEY: SITE
<222> LOCATION: (15)
<223> OTHER INFORMATION: Tyr is D-Tyr

<400> SEQUENCE: 115

Tyr Xaa Xaa Xaa Arg Arg Arg Gln Arg Arg Lys Lys Arg Gly Tyr
1               5                   10                  15

<210> SEQ ID NO 116
<211> LENGTH: 4
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (3)..(4)
<223> OTHER INFORMATION: Positions 3 to 4 are D-amino acids
<220> FEATURE:
<221> NAME/KEY: SITE
<222> LOCATION: (2)
<223> OTHER INFORMATION: Xaa is aminoundecanoic acid
<220> FEATURE:
<221> NAME/KEY: SITE
<222> LOCATION: (3)
<223> OTHER INFORMATION: Xaae is D-Phenylalanine-2,3,4,5,6-F
```

```
<220> FEATURE:
<221> NAME/KEY: SITE
<222> LOCATION: (4)
<223> OTHER INFORMATION: Xaa is D-Cyclohexyl-alanine

<400> SEQUENCE: 116

Tyr Xaa Xaa Xaa
1

<210> SEQ ID NO 117
<211> LENGTH: 14
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (2)   (12)
<223> OTHER INFORMATION: Positions 2 to 12 are D-amino acids
<220> FEATURE:
<221> NAME/KEY: SITE
<222> LOCATION: (1)
<223> OTHER INFORMATION: Xaa is aminoundecanoic acid
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (3)
<223> OTHER INFORMATION: Xaa is D-Cyclohexyl-alanine
<220> FEATURE:
<221> NAME/KEY: SITE
<222> LOCATION: (14)
<223> OTHER INFORMATION: Tyr is D-Tyr

<400> SEQUENCE: 117

Xaa Xaa Xaa Arg Arg Arg Gln Arg Arg Lys Lys Arg Gly Tyr
1               5                   10

<210> SEQ ID NO 118
<211> LENGTH: 3
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (2)..(3)
<223> OTHER INFORMATION: Positions 2 to 3 are D-amino acids
<220> FEATURE:
<221> NAME/KEY: SITE
<222> LOCATION: (1)
<223> OTHER INFORMATION: Xaa is aminoundecanoic acid
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (3)
<223> OTHER INFORMATION: Xaa is D-Cyclohexyl-alanine

<400> SEQUENCE: 118

Xaa Xaa Xaa
1

<210> SEQ ID NO 119
<211> LENGTH: 9
<212> TYPE: PRT
<213> ORGANISM: Artificial sequence
```

-continued

```
<220> FEATURE:
<223> OTHER INFORMATION: Description of artificial sequence: Synthetic
      peptide
<220> FEATURE:
<221> NAME/KEY: SITE
<222> LOCATION: (2)..(9)
<223> OTHER INFORMATION: Positions 2 to 9 are D-amino acids
<220> FEATURE:
<221> NAME/KEY: SITE
<222> LOCATION: (1)
<223> OTHER INFORMATION: Xaa is aminoundecanoic acid
<220> FEATURE:
<221> NAME/KEY: SITE
<222> LOCATION: (2)
<223> OTHER INFORMATION: Xaa is D-Phenylalanine-2,3,4,5,6-F
<220> FEATURE:
<221> NAME/KEY: SITE
<222> LOCATION: (3)
<223> OTHER INFORMATION: Xaa is D-Cyclohexyl-alanine

<400> SEQUENCE: 119

Xaa Xaa Xaa Arg Arg Arg Gln Arg Arg
1               5

<210> SEQ ID NO 120
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (2)..(9)
<223> OTHER INFORMATION: Positions 2 to 9 are D-amino acids
<220> FEATURE:
<221> NAME/KEY: SITE
<222> LOCATION: (1)
<223> OTHER INFORMATION: Xaa is 8-aminocaprylic acid
<220> FEATURE:
<221> NAME/KEY: SITE
<222> LOCATION: (2)
<223> OTHER INFORMATION: Xaa is D-Cyclohexyl-alanine
<220> FEATURE:
<221> NAME/KEY: SITE
<222> LOCATION: (3)
<223> OTHER INFORMATION: Xaa is D-Phenylalanine-2,3,4,5,6-F

<400> SEQUENCE: 120

Xaa Xaa Xaa Arg Arg Arg Gln Arg Arg
1               5

<210> SEQ ID NO 121
<211> LENGTH: 2
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (1)
<223> OTHER INFORMATION: Xaa is D-Phenylalanine-2,3,4,5,6-F
<220> FEATURE:
<221> NAME/KEY: SITE
<222> LOCATION: (2)
<223> OTHER INFORMATION: Xaa is D-Cyclohexyl-alanine

<400> SEQUENCE: 121

Xaa Xaa
```

SEQ ID NO 122
LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (1)
<223> OTHER INFORMATION: Xaa is D-Cyclohexyl-alanine
<220> FEATURE:
<221> NAME/KEY: SITE
<222> LOCATION: (2)
<223> OTHER INFORMATION: Xaa is D-Phenylalanine-2,3,4,5,6-F

<400> SEQUENCE: 122

Xaa Xaa Arg Arg Arg Gln Arg Arg
    1               5

SEQ ID NO 123
LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 123

Tyr Ser Ser Trp Ser Xaa Xaa Arg Arg Arg Gln Arg Arg
    1               5                   10

SEQ ID NO 124
LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (2)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

```
<400> SEQUENCE: 124

Tyr Xaa Ser Trp Ser Xaa Xaa Arg Arg Arg Gln Arg Arg
1               5                   10

<210> SEQ ID NO 125
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)
<223> OTHER INFORMATION: Xaa is D-Cyclohexyl-alanine
<220> FEATURE:
<221> NAME/KEY: SITE
<222> LOCATION: (4)
OTHER INFORMATION: Xaa is D-Phenylalanine-2,3,4,5,6-F

<400> SEQUENCE: 125

Xaa Xaa Xaa Xaa Arg Arg Arg Gln Arg Arg
1               5                   10

<210> SEQ ID NO 126
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)
<223> OTHER INFORMATION: Xaa is D-Phenylalanine-2,3,4,5,6-F
<220> FEATURE:
<221> NAME/KEY: SITE
<222> LOCATION: (4)
OTHER INFORMATION: Xaa is D-Cyclohexyl-alanine

<400> SEQUENCE: 126

Xaa Xaa Xaa Xaa Arg Arg Arg Gln Arg Arg
1               5                   10

<210> SEQ ID NO 127
<211> LENGTH: 13
<212> TYPE: PRT
<213> ORGANISM: Artificial sequence
<220> FEATURE:
```

```
<223> OTHER INFORMATION: Description of artificial sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (2)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 127

Asp Xaa Ser Trp Ser Xaa Xaa Arg Arg Arg Gln Arg Arg
1               5                   10

<210> SEQ ID NO 128
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 128

Xaa Asp Ser Trp Ser Xaa Xaa Arg Arg Arg Gln Arg Arg
1               5                   10

<210> SEQ ID NO 129
<211> LENGTH: 13
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine
```

```
<400> SEQUENCE: 129

Xaa Ser Trp Ser Asp Xaa Xaa Arg Arg Arg Gln Arg Arg
1               5                   10

<210> SEQ ID NO 130
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Benzoyl-phenylalanine
<220> FEATURE:
<221> NAME/KEY: SITE
<222> LOCATION: (6)
<223> OTHER INFORMATION: Xaa is D-Cyclohexyl-alanine

<400> SEQUENCE: 130

Xaa Ser Trp Ser Xaa Xaa Arg Arg Arg Gln Arg Arg
1               5                   10

<210> SEQ ID NO 131
<211> LENGTH: 10
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)
<223> OTHER INFORMATION: Xaa is D-Benzoyl-phenylalanine
<220> FEATURE:
<221> NAME/KEY: SITE
<222> LOCATION: (4)
OTHER INFORMATION: Xaa is D-Cyclohexyl-alanine

<400> SEQUENCE: 131

Xaa Xaa Xaa Xaa Arg Arg Arg Gln Arg Arg
1               5                   10

<210> SEQ ID NO 132
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
```

```
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-4NO2
<220> FEATURE:
<221> NAME/KEY: SITE
<222> LOCATION: (6)
<223> OTHER INFORMATION: Xaa is D-Cyclohexyl-alanine

<400> SEQUENCE: 132

Xaa Pro Trp Pro Xaa Xaa Arg Arg Arg Gln Arg Arg
1               5                   10

<210> SEQ ID NO 133
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-4NO2
<220> FEATURE:
<221> NAME/KEY: SITE
<222> LOCATION: (6)
<223> OTHER INFORMATION: Xaa is D-2-Naphthyl-alanyl

<400> SEQUENCE: 133

Xaa Pro Trp Pro Xaa Xaa Arg Arg Arg Gln Arg Arg
1               5                   10

<210> SEQ ID NO 134
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)
<223> OTHER INFORMATION: Xaa is D-Phenylalanine-4NO2
<220> FEATURE:
<221> NAME/KEY: SITE
<222> LOCATION: (5)
<223> OTHER INFORMATION: Xaa is D-Phenylalanine-4NO2
<220> FEATURE:
<221> NAME/KEY: SITE
<222> LOCATION: (6)
<223> OTHER INFORMATION: Xaa is D-Cyclohexyl-alanine

<400> SEQUENCE: 134

Xaa Pro Trp Pro Xaa Xaa Arg Arg Arg Gln Arg Arg
1               5                   10
```

```
<210> SEQ ID NO 135
<211> LENGTH: 7
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(7)
<223> OTHER INFORMATION: Positions 1 to 7 are D-amino acids
<220> FEATURE:
<221> NAME/KEY: SITE
<222> LOCATION: (1)
<223> OTHER INFORMATION: Xaa is D-Benzoyl-phenylalanine
<220> FEATURE:
<221> NAME/KEY: SITE
<222> LOCATION: (5)
<223> OTHER INFORMATION: Xaa is D-Phenylalanine-2,3,4,5,6-F
<220> FEATURE:
<221> NAME/KEY: SITE
<222> LOCATION: (6)
<223> OTHER INFORMATION: Xaa is D-Cyclohexyl-alanine

<400> SEQUENCE: 135

Xaa Cys Trp Arg Xaa Xaa Cys
1               5

<210> SEQ ID NO 136
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (6)
<223> OTHER INFORMATION: Xaa is D-Phenylalanine-2,3,4,5,6-F
<220> FEATURE:
<221> NAME/KEY: SITE
<222> LOCATION: (7)
<223> OTHER INFORMATION: Xaa is D-Cyclohexyl-alanine

<400> SEQUENCE: 136

Tyr Cys Pro Trp Arg Xaa Xaa Cys
1               5

SEQ ID NO 137

<400> SEQUENCE: 137

000

<210> SEQ ID NO 138
<211> LENGTH: 9
<212> TYPE: PRT
<213> ORGANISM: Artificial sequence
<220> FEATURE:
<223> OTHER INFORMATION: Description of artificial sequence: Synthetic
      peptide

<400> SEQUENCE: 138

Tyr Gly Gly Pro Gly Gly Gly Gly Asn
1               5
```

```
<210> SEQ ID NO 139
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 139

Arg Tyr Ser Leu Pro Pro Glu Leu Ser Asn Met
1               5                   10

<210> SEQ ID NO 140
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 140

Leu Ala Arg Ser Ala Ser Met Pro Glu Ala Leu
1               5                   10

<210> SEQ ID NO 141
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 141

Leu Tyr Arg Ser Pro Ser Met Pro Glu Asn Leu
1               5                   10

<210> SEQ ID NO 142
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 142

Leu Tyr Arg Ser Pro Ala Met Pro Glu Asn Leu
1               5                   10

<210> SEQ ID NO 143
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 143

Trp Tyr Arg Ser Pro Ser Phe Tyr Glu Asn Leu
1               5                   10

<210> SEQ ID NO 144
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 144
```

Trp Tyr Arg Ser Pro Ser Tyr Tyr Glu Asn Leu
1               5                   10

<210> SEQ ID NO 145
<211> LENGTH: 8
<212> TYPE: PRT
<213> ORGANISM: Artificial sequence
<220> FEATURE:
<223> OTHER INFORMATION: Description of artificial sequence: Synthetic
      peptide

<400> SEQUENCE: 145

Trp Tyr Arg Ser Pro Ser Tyr Tyr
1               5

<210> SEQ ID NO 146
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 146

Leu Tyr Arg Ser Pro Ser Tyr Pro Glu Asn Leu
1               5                   10

<210> SEQ ID NO 147
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 147

Leu Tyr Arg Ser Pro Ser Tyr Phe Glu Asn Leu
1               5                   10

<210> SEQ ID NO 148
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 148

Leu Tyr Arg Ser Pro Ser Tyr Tyr Glu Asn Leu
1               5                   10

<210> SEQ ID NO 149
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 149

Leu Tyr Arg Ser Pro Ser Tyr Trp Glu Asn Leu
1               5                   10

<210> SEQ ID NO 150
<211> LENGTH: 11
<212> TYPE: PRT
<213> ORGANISM: Artificial sequence -continued

```
<220> FEATURE:
<223> OTHER INFORMATION: Description of artificial sequence: Synthetic
      peptide

<400> SEQUENCE: 150

Leu Tyr Arg Ser Pro Ser Asn Pro Glu Asn Leu
1               5                   10

<210> SEQ ID NO 151
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 151

Leu Tyr Arg Ser Pro Ser Asn Phe Glu Asn Leu
1               5                   10

<210> SEQ ID NO 152
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 152

Leu Tyr Arg Ser Pro Ser Asn Tyr Glu Asn Leu
1               5                   10

<210> SEQ ID NO 153
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 153

Leu Tyr Arg Ser Pro Ser Asn Trp Glu Asn Leu
1               5                   10

<210> SEQ ID NO 154
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 154

Leu Tyr Arg Ser Pro Ser His Pro Glu Asn Leu
1               5                   10

<210> SEQ ID NO 155
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 155

Leu Tyr Arg Ser Pro Ser His Phe Glu Asn Leu
1               5                   10
```

```
<210> SEQ ID NO 156
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 156

Leu Tyr Arg Ser Pro Ser His Tyr Glu Asn Leu
1               5                   10

<210> SEQ ID NO 157
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 157

Leu Tyr Arg Ser Pro Ser His Trp Glu Asn Leu
1               5                   10

<210> SEQ ID NO 158
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 158

Leu Tyr Ser Ser Pro Ser Met Pro Glu Asn Leu
1               5                   10

<210> SEQ ID NO 159
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 159

Leu Tyr Ser Ser Pro Ser Met Phe Glu Asn Leu
1               5                   10

<210> SEQ ID NO 160
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 160

Leu Tyr Ser Ser Pro Ser Met Tyr Glu Asn Leu
1               5                   10

<210> SEQ ID NO 161
<211> LENGTH: 11
<212> TYPE: PRT
<213> ORGANISM: Artificial sequence
<220> FEATURE:
<223> OTHER INFORMATION: Description of artificial sequence: Synthetic
      peptide
```

```
<400> SEQUENCE: 161

Leu Tyr Ser Ser Pro Ser Met Trp Glu Asn Leu
1               5                   10

<210> SEQ ID NO 162
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 162

Leu Tyr Ser Ser Pro Ser Phe Pro Glu Asn Leu
1               5                   10

<210> SEQ ID NO 163
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 163

Leu Tyr Ser Ser Pro Ser Phe Pro Glu Asn Leu
1               5                   10

<210> SEQ ID NO 164
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 164

Leu Tyr Ser Ser Pro Ser Phe Phe Glu Asn Leu
1               5                   10

<210> SEQ ID NO 165
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 165

Leu Tyr Ser Ser Pro Ser Phe Tyr Glu Asn Leu
1               5                   10

<210> SEQ ID NO 166
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 166

Leu Tyr Ser Ser Pro Ser Phe Trp Glu Asn Leu
1               5                   10

<210> SEQ ID NO 167
<211> LENGTH: 11
<212> TYPE: PRT
```

```
<213> ORGANISM: Artificial sequence
<220> FEATURE:
<223> OTHER INFORMATION: Description of artificial sequence: Synthetic
      peptide

<400> SEQUENCE: 167

Leu Tyr Ser Ser Pro Ser Tyr Pro Glu Asn Leu
1               5                   10

<210> SEQ ID NO 168
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 168

Leu Tyr Ser Ser Pro Ser Tyr Phe Glu Asn Leu
1               5                   10

<210> SEQ ID NO 169
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 169

Leu Tyr Ser Ser Pro Ser Tyr Tyr Glu Asn Leu
1               5                   10

<210> SEQ ID NO 170
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 170

Leu Tyr Ser Ser Pro Ser Tyr Trp Glu Asn Leu
1               5                   10

<210> SEQ ID NO 171
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 171

Leu Tyr Ser Ser Pro Ser Gln Pro Glu Asn Leu
1               5                   10

<210> SEQ ID NO 172
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 172

Leu Tyr Ser Ser Pro Ser Gln Trp Glu Asn Leu
1               5                   10
```

<210> SEQ ID NO 173
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 173

Leu Tyr Ser Ser Pro Ser His Pro Glu Asn Leu
1               5                   10

<210> SEQ ID NO 174
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 174

Leu Tyr Ser Ser Pro Ser His Phe Glu Asn Leu
1               5                   10

<210> SEQ ID NO 175
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 175

Leu Tyr Ser Ser Pro Ser His Tyr Glu Asn Leu
1               5                   10

<210> SEQ ID NO 176
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 176

Leu Tyr Ser Ser Pro Ser His Trp Glu Asn Leu
1               5                   10

<210> SEQ ID NO 177
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 177

Leu Tyr Thr Ser Pro Ser Met Pro Glu Asn Leu
1               5                   10

<210> SEQ ID NO 178
<211> LENGTH: 11
<212> TYPE: PRT
<213> ORGANISM: Artificial sequence
<220> FEATURE:
<223> OTHER INFORMATION: Description of artificial sequence: Synthetic
      peptide

```
<400> SEQUENCE: 178

Leu Tyr Thr Ser Pro Ser Met Phe Glu Asn Leu
1               5                   10

<210> SEQ ID NO 179
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 179

Leu Tyr Thr Ser Pro Ser Met Tyr Glu Asn Leu
1               5                   10

<210> SEQ ID NO 180
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 180

Leu Tyr Thr Ser Pro Ser Met Trp Glu Asn Leu
1               5                   10

<210> SEQ ID NO 181
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 181

Leu Tyr Thr Ser Pro Ser Phe Pro Glu Asn Leu
1               5                   10

<210> SEQ ID NO 182
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 182

Leu Tyr Thr Ser Pro Ser Phe Phe Glu Asn Leu
1               5                   10

<210> SEQ ID NO 183
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 183

Leu Tyr Thr Ser Pro Ser Phe Tyr Glu Asn Leu
1               5                   10

<210> SEQ ID NO 184
<211> LENGTH: 11
```

```
<212> TYPE: PRT
<213> ORGANISM: Artificial sequence
<220> FEATURE:
<223> OTHER INFORMATION: Description of artificial sequence: Synthetic
      peptide

<400> SEQUENCE: 184

Leu Tyr Thr Ser Pro Ser Phe Trp Glu Asn Leu
1               5                   10

<210> SEQ ID NO 185
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 185

Leu Tyr Thr Ser Pro Ser Tyr Pro Glu Asn Leu
1               5                   10

<210> SEQ ID NO 186
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 186

Leu Tyr Thr Ser Pro Ser Tyr Phe Glu Asn Leu
1               5                   10

<210> SEQ ID NO 187
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 187

Leu Tyr Thr Ser Pro Ser Tyr Tyr Glu Asn Leu
1               5                   10

<210> SEQ ID NO 188
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 188

Leu Tyr Thr Ser Pro Ser Tyr Trp Glu Asn Leu
1               5                   10

<210> SEQ ID NO 189
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 189

Leu Tyr Thr Ser Pro Ser Asn Pro Glu Asn Leu
```

-continued

```
<210> SEQ ID NO 190
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 190

Leu Tyr Thr Ser Pro Ser Asn Phe Glu Asn Leu
1               5                   10

<210> SEQ ID NO 191
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 191

Leu Tyr Thr Ser Pro Ser Asn Tyr Glu Asn Leu
1               5                   10

<210> SEQ ID NO 192
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 192

Leu Tyr Thr Ser Pro Ser Asn Trp Glu Asn Leu
1               5                   10

<210> SEQ ID NO 193
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 193

Leu Tyr Thr Ser Pro Ser His Pro Glu Asn Leu
1               5                   10

<210> SEQ ID NO 194
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 194

Leu Tyr Thr Ser Pro Ser His Phe Glu Asn Leu
1               5                   10

<210> SEQ ID NO 195
<211> LENGTH: 11
<212> TYPE: PRT
<213> ORGANISM: Artificial sequence
<220> FEATURE:
<223> OTHER INFORMATION: Description of artificial sequence: Synthetic
```

```
              peptide

<400> SEQUENCE: 195

Leu Tyr Thr Ser Pro Ser His Tyr Glu Asn Leu
1               5                   10

<210> SEQ ID NO 196
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 196

Leu Tyr Thr Ser Pro Ser His Trp Glu Asn Leu
1               5                   10

<210> SEQ ID NO 197
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 197

Leu Tyr His Ser Pro Ser Tyr Pro Glu Asn Leu
1               5                   10

<210> SEQ ID NO 198
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 198

Leu Tyr His Ser Pro Ser Tyr Phe Glu Asn Leu
1               5                   10

<210> SEQ ID NO 199
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 199

Leu Tyr His Ser Pro Ser Tyr Tyr Glu Asn Leu
1               5                   10

<210> SEQ ID NO 200
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 200

Leu Tyr His Ser Pro Ser Tyr Trp Glu Asn Leu
1               5                   10

<210> SEQ ID NO 201
```

```
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 201

Leu Phe Thr Ser Pro Ser Tyr Pro Glu Asn Leu
1               5                   10

<210> SEQ ID NO 202
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 202

Leu Phe Thr Ser Pro Ser Tyr Phe Glu Asn Leu
1               5                   10

<210> SEQ ID NO 203
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 203

Leu Phe Thr Ser Pro Ser Tyr Tyr Glu Asn Leu
1               5                   10

<210> SEQ ID NO 204
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 204

Leu Phe Thr Ser Pro Ser Tyr Trp Glu Asn Leu
1               5                   10

<210> SEQ ID NO 205
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 205

Phe Tyr Ser Ser Pro Ser His Pro Glu Asn Leu
1               5                   10

<210> SEQ ID NO 206
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 206
```

```
Phe Tyr Ser Ser Pro Ser His Phe Glu Asn Leu
1               5                   10

<210> SEQ ID NO 207
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 207

Phe Tyr Ser Ser Pro Ser His Tyr Glu Asn Leu
1               5                   10

<210> SEQ ID NO 208
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 208

Phe Tyr Ser Ser Pro Ser His Trp Glu Asn Leu
1               5                   10

<210> SEQ ID NO 209
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 209

Phe Tyr Thr Ser Pro Ser Met Pro Glu Asn Leu
1               5                   10

<210> SEQ ID NO 210
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 210

Phe Tyr Thr Ser Pro Ser Met Phe Glu Asn Leu
1               5                   10

<210> SEQ ID NO 211
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 211

Phe Tyr Thr Ser Pro Ser Met Tyr Glu Asn Leu
1               5                   10

<210> SEQ ID NO 212
<211> LENGTH: 11
<212> TYPE: PRT
<213> ORGANISM: Artificial sequence
<220> FEATURE:
```

<223> OTHER INFORMATION: Description of artificial sequence: Synthetic
      peptide

<400> SEQUENCE: 212

Phe Tyr Thr Ser Pro Ser Met Trp Glu Asn Leu
1               5                   10

<210> SEQ ID NO 213
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 213

Phe Tyr Thr Ser Pro Ser Phe Pro Glu Asn Leu
1               5                   10

<210> SEQ ID NO 214
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 214

Phe Tyr Thr Ser Pro Ser Phe Phe Glu Asn Leu
1               5                   10

<210> SEQ ID NO 215
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 215

Phe Tyr Thr Ser Pro Ser Phe Tyr Glu Asn Leu
1               5                   10

<210> SEQ ID NO 216
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 216

Phe Tyr Thr Ser Pro Ser Phe Trp Glu Asn Leu
1               5                   10

<210> SEQ ID NO 217
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 217

Phe Tyr Thr Ser Pro Ser Tyr Pro Glu Asn Leu
1               5                   10

```
<210> SEQ ID NO 218
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 218

Phe Tyr Thr Ser Pro Ser Tyr Phe Glu Asn Leu
1               5                   10

<210> SEQ ID NO 219
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 219

Phe Tyr Thr Ser Pro Ser Tyr Tyr Glu Asn Leu
1               5                   10

<210> SEQ ID NO 220
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 220

Phe Tyr Thr Ser Pro Ser Tyr Trp Glu Asn Leu
1               5                   10

<210> SEQ ID NO 221
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 221

Trp Tyr Arg Ser Pro Ser Met Pro Glu Asn Leu
1               5                   10

<210> SEQ ID NO 222
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 222

Trp Tyr Arg Ser Pro Ser Met Phe Glu Asn Leu
1               5                   10

<210> SEQ ID NO 223
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 223
```

-continued

Trp Tyr Arg Ser Pro Ser Met Tyr Glu Asn Leu
1               5                   10

<210> SEQ ID NO 224
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 224

Trp Tyr Arg Ser Pro Ser Met Trp Glu Asn Leu
1               5                   10

<210> SEQ ID NO 225
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 225

Trp Tyr Arg Ser Pro Ser Phe Pro Glu Asn Leu
1               5                   10

<210> SEQ ID NO 226
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 226

Trp Tyr Arg Ser Pro Ser Phe Phe Glu Asn Leu
1               5                   10

<210> SEQ ID NO 227
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 227

Trp Tyr Arg Ser Pro Ser Phe Tyr Glu Asn Leu
1               5                   10

<210> SEQ ID NO 228
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 228

Trp Tyr Arg Ser Pro Ser Phe Trp Glu Asn Leu
1               5                   10

<210> SEQ ID NO 229
<211> LENGTH: 11
<212> TYPE: PRT
<213> ORGANISM: Artificial sequence

```
<220> FEATURE:
<223> OTHER INFORMATION: Description of artificial sequence: Synthetic
      peptide

<400> SEQUENCE: 229

Trp Tyr Arg Ser Pro Ser Tyr Pro Glu Asn Leu
1               5                   10

<210> SEQ ID NO 230
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 230

Trp Tyr Arg Ser Pro Ser Tyr Phe Glu Asn Leu
1               5                   10

<210> SEQ ID NO 231
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 231

Trp Tyr Arg Ser Pro Ser Tyr Tyr Glu Asn Leu
1               5                   10

<210> SEQ ID NO 232
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 232

Trp Tyr Arg Ser Pro Ser Tyr Trp Glu Asn Leu
1               5                   10

<210> SEQ ID NO 233
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 233

Trp Tyr Thr Ser Pro Ser Met Pro Glu Asn Leu
1               5                   10

<210> SEQ ID NO 234
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 234

Trp Tyr Thr Ser Pro Ser Met Phe Glu Asn Leu
1               5                   10
```

<210> SEQ ID NO 235
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 235

Trp Tyr Thr Ser Pro Ser Met Tyr Glu Asn Leu
1               5                   10

<210> SEQ ID NO 236
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 236

Trp Tyr Thr Ser Pro Ser Met Trp Glu Asn Leu
1               5                   10

<210> SEQ ID NO 237
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 237

Trp Tyr Thr Ser Pro Ser Phe Pro Glu Asn Leu
1               5                   10

<210> SEQ ID NO 238
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 238

Trp Tyr Thr Ser Pro Ser Phe Phe Glu Asn Leu
1               5                   10

<210> SEQ ID NO 239
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 239

Trp Tyr Thr Ser Pro Ser Phe Tyr Glu Asn Leu
1               5                   10

<210> SEQ ID NO 240
<211> LENGTH: 11
<212> TYPE: PRT
<213> ORGANISM: Artificial sequence
<220> FEATURE:
<223> OTHER INFORMATION: Description of artificial sequence: Synthetic
      peptide

```
<400> SEQUENCE: 240

Trp Tyr Thr Ser Pro Ser Phe Trp Glu Asn Leu
1               5                   10

<210> SEQ ID NO 241
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 241

Trp Tyr Thr Ser Pro Ser Tyr Pro Glu Asn Leu
1               5                   10

<210> SEQ ID NO 242
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 242

Trp Tyr Thr Ser Pro Ser Tyr Phe Glu Asn Leu
1               5                   10

<210> SEQ ID NO 243
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 243

Trp Tyr Thr Ser Pro Ser Tyr Tyr Glu Asn Leu
1               5                   10

<210> SEQ ID NO 244
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 244

Trp Tyr Thr Ser Pro Ser Tyr Trp Glu Asn Leu
1               5                   10

<210> SEQ ID NO 245
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 245

Trp Tyr Thr Ser Pro Ser His Pro Glu Asn Leu
1               5                   10

<210> SEQ ID NO 246
<211> LENGTH: 11
<212> TYPE: PRT
```

-continued

<213> ORGANISM: Artificial sequence
<220> FEATURE:
<223> OTHER INFORMATION: Description of artificial sequence: Synthetic
      peptide

<400> SEQUENCE: 246

Trp Tyr Thr Ser Pro Ser His Phe Glu Asn Leu
1               5                   10

<210> SEQ ID NO 247
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 247

Trp Tyr Thr Ser Pro Ser His Tyr Glu Asn Leu
1               5                   10

<210> SEQ ID NO 248
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 248

Trp Tyr Thr Ser Pro Ser His Trp Glu Asn Leu
1               5                   10

<210> SEQ ID NO 249
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 249

Leu Lys Arg Ser Pro Ser Met Pro Glu Asn Leu
1               5                   10

<210> SEQ ID NO 250
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 250

Leu Tyr Ile Ser Pro Ser Met Pro Glu Asn Leu
1               5                   10

<210> SEQ ID NO 251
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 251

Leu Tyr Arg Ser Pro Ser Met Val Glu Asn Leu
1               5                   10

```
<210> SEQ ID NO 252
<211> LENGTH: 11
<212> TYPE: PRT
<213> ORGANISM: Artificial sequence
<220> FEATURE:
<223> OTHER INFORMATION: Description of artificial sequence: Synthetic
      peptide

<400> SEQUENCE: 252

Tyr Gly Arg Lys Lys Arg Arg Gln Arg Arg Arg
1               5                   10

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000
```